(12) United States Patent
Sfez et al.

(10) Patent No.: US 6,815,694 B2
(45) Date of Patent: Nov. 9, 2004

(54) APPARATUS AND METHOD FOR PROBING LIGHT ABSORBING AGENTS IN BIOLOGICAL TISSUES

(75) Inventors: Bruno Gad Sfez, Jerusalem (IL); Aner Lev, Modiin (IL); Zvi Kotler, Tel Aviv (IL)

(73) Assignee: The State of Israel Atomic Energy Commission Soreq Nuclear Research Center, Yavne (IL)

( * ) Notice: Subject to any disclaimer, the term of this patent is extended or adjusted under 35 U.S.C. 154(b) by 30 days.

(21) Appl. No.: 10/333,684

(22) PCT Filed: Jul. 23, 2001

(86) PCT No.: PCT/IL01/00674
§ 371 (c)(1),
(2), (4) Date: Jan. 23, 2003

(87) PCT Pub. No.: WO02/08740
PCT Pub. Date: Jan. 31, 2002

(65) Prior Publication Data
US 2004/0099815 A1 May 27, 2004

(30) Foreign Application Priority Data
Jul. 23, 2000 (IL) ................................................ 137447

(51) Int. Cl.[7] ................................................ A61B 5/00
(52) U.S. Cl. ...................... 250/492.1; 600/407; 73/957; 73/597; 367/7; 356/340
(58) Field of Search ...................... 250/492.1; 600/407; 73/957, 597; 367/7; 356/340

(56) References Cited

U.S. PATENT DOCUMENTS

| | | |
|---|---|---|
| 4,587,972 A | 5/1986 | Morantte, Jr. |
| 5,174,298 A | 12/1992 | Dolfi et al. |
| 5,212,667 A | 5/1993 | Tomlinson, Jr. et al. |
| 5,286,968 A | 2/1994 | Fournier et al. |
| 5,293,873 A | 3/1994 | Fang |

(List continued on next page.)

FOREIGN PATENT DOCUMENTS

| | | |
|---|---|---|
| DE | 44 19 900 A1 | 12/1995 |
| EP | 0 832599 A1 | 4/1998 |
| WO | WO 89/00278 A1 | 1/1989 |
| WO | WO 95/33987 A1 | 12/1995 |

OTHER PUBLICATIONS

Kempe et al., "Acousto–Optic Tomography With Multiply Scattered Light", *J. Opt. Soc. Am. A*, vol. 14, No. 5, pp. 1151–1158 (May 1997).

(List continued on next page.)

*Primary Examiner*—John R. Lee
*Assistant Examiner*—Zia R. Hashmi
(74) *Attorney, Agent, or Firm*—Browdy and Neimark, P.L.L.C.

(57) ABSTRACT

A method and apparatus are presented for detecting an effect of interactions of electromagnetic radiation with ultrasound radiation at different locations within a region of interest in a scattering medium to thereby enable imaging of said medium. A plurality of sequences of pulses of ultrasound radiation is transmitted towards a plurality of locations, respectively, in said region of interest within an X-Y plane perpendicular to axes of propagation of the ultrasound pulses. Said region of interest is illuminated with incident electromagnetic radiation of at least one wavelength. The phases of the ultrasound radiation or the phases of the electromagnetic radiation components are appropriately controlled in order to be enable identification of the interactions between the electromagnetic and ultrasound radiation that occur at different locations along the Z-axis. Signals of the electromagnetic radiation, each being frequency modulated by a frequency of the ultrasound radiation, are detected, to thereby enabling the imaging of the region of interest.

26 Claims, 26 Drawing Sheets

U.S. PATENT DOCUMENTS

| | | |
|---|---|---|
| 5,713,356 A | 2/1998 | Kruger |
| 5,801,312 A | 9/1998 | Lorraine et al. |
| 5,951,481 A | 9/1999 | Evans |
| 6,041,248 A | 3/2000 | Wang |

OTHER PUBLICATIONS

Ishimaru, *Wave Propagation and Scattering in Random Media*, "volume 1: Single Scattering and Transport Theory", pp. 63–67, Academic Press, Inc. (1978).

Pine et al., "Dynamical Correlations of Multiply Scattered Light", *Scattering and Localization of Classical Waves In Random Media*, Ping Sheng, ed., World Scientific, pp. 312–371 (1990).

Leutz et al., "Ultrasonic Modulation of multiply Scattered Light", *Physica B*, vol. 204, pp. 14–19 (1995).

Mahan et al., "Ultrasonic Tagging of Light: Theory", *Proc. Natl. Acad. Sci. USA*, vol. 95, pp. 14015–14019 (Nov. 1998).

Marks et al., "A Comprehensive Approach to breast Cancer Detection using Light: Photon Localization By Ultrasound modulation and Tissue Characterization By Spectral Discrimination", *Proceedings of the SPIE*, SPIE, Bellingham, VA, No. 1888, pp. 500–510 (Jan. 17, 1993).

APPARATUS AND METHOD FOR PROBING LIGHT ABSORBING AGENTS IN BIOLOGICAL TISSUES

FIELD OF THE INVENTION

This invention is generally in the field of non-invasive measurement techniques, and relates to a process and apparatus for real-time imaging and sensing (probing) light absorbing agents, such as hemoglobin, in biological tissues.

The following is a list of some prior art patents, documents and articles which are relevant for the better understanding of the background of the invention, as will be described further below:

List of References

1. A. Ishimaru, "*Wave Propagation and Scattering in Random Media*", Vol. 1, Academic Press (1978)
2. M. Kempe et al., "*Acousto-optic tomography with multiply scattered light*", J. Opt. Soc. A., 14, 5, 1151 (1997)
3. WO 89/00278
4. U.S. Pat. No. 5,174,298
5. U.S. Pat. No. 5,286,968
6. U.S. Pat. No. 5,212,667
7. U.S. Pat. No. 5,951,481
8. U.S. Pat. No. 6,041,248
9. WO 95/33987
10. Fay A. Marks et al, "*Comprehensive approach to breast cancer detection using light: photon localization by ultrasound modulation and tissue characterization by spectral discrimination*", SPIE, vol. 1888, pp.500–509.
11. G. D. Mahan et al., "*Ultrasonic tagging of light: theory*", Proc. Natl. Acad. Sci. USA, 95, 14015, (1998).
12. D. J. Pine et al. "*Dynamical correlations of multiply-scattered light*", Scattering and Localization of Classical Waves in Random Media, Ping Sheng ed. World Scientific (1990).
13. W. Leutz and G. Maret, "*Ultrasonic modulation of multiply scattered light*", Physica B, 204, 14–19, (1995).

BACKGROUND OF THE INVENTION

In recent years, much effort has been devoted to find a technique alternative to Magnetic Resonance Imaging (MRI) or Computed Tomography (CT) for non-invasively probing living biological tissues, such as body organs. MRI and CT involve long procedures and do not always allow real time analysis of measured data. Low-cost, portable and easy-to-use devices have been developed based on near infrared spectroscopy of blood (e.g., pulse oximetry). This technique, however, provides only a global picture of the tissues with a resolution that does not allow functional imaging of the tissue and a reliable diagnosis.

It is well-known that hemoglobin can be found in the body in two different oxygenation states—oxyhemoglobin and deoxyhemoglobin—which have different light absorption spectra (A. Ishimaru, "*Wave Propagation and Scattering in Random Media*", Vol. 1, Academic Press (1978)). In the near infrared range, (690–900 nm), the absorption coefficients of both states of hemoglobin are relatively low. At around 804 mm, both states have exactly the same absorption coefficient, and this point is called "the isosbestic point". Therefore, measurement of blood absorption at this wavelength gives a direct indication of the blood volume being tested. At longer wavelengths, the absorption is essentially due to oxyhemoglobin. For example, at or around light wavelengths of 1 micron, the absorption of oxyhemoglobin is more than three times higher than that of the deoxyhemoglobin. Hence, absorption at these wavelengths (0.804 $\mu$m and 1 $\mu$m) gives a direct indication of the ratio between the two states of hemoglobin.

Hemoglobin oxygenation provides insight on the proper functioning of many body organs such as the brain, breast, liver, heart, etc. Other agents, such as indocyanin green, present absorption in a definite region in the near-infrared range, and can be probed also using infrared light, deeply inside the tissues.

Light propagating inside a scattering medium has two components—ballistic and diffuse light. The first component does not experience scattering, while the second corresponds to strongly multi-scattered light (M. Kempe et al., "*Acousto-optic tomography with multiply scattered light*", J. Opt. Soc. A., 14, 5, 1151 (1997)). Ballistic light intensity decreases with distance in a scattering medium much more than that of the diffuse light. Therefore, diffuse light can provide information on a scattering medium deep inside it.

It is known in the art to use the diffuse (scattered) light to obtain information on the optical properties of the medium. This is implemented by utilizing an ultrasound wave focused on the particular region under examination inside the medium. Generally, this technique consists of the following: If an ultrasound wave propagates through a region in a scattering medium and an electromagnetic wave (such as a laser light beam) crosses said region and is strongly diffused thereby, the electromagnetic wave frequency is shifted by the frequency of the ultrasound wave (acousto-optic effect) at the location of said region. In other regions, where no interaction between the light and ultrasound waves occurs, the frequency of light is unchanged, and consequently, the detection of the frequency-shifted electromagnetic wave gives direct information on the absorption properties of said region.

WO 89/00278 discloses a technique of ultrasound tagging of light utilizing a continuous ultrasound wave. The manner in which this tagging of light is to be done is, however, physically difficult to implement, since the light detection is obtained using a photo-refractive crystal that requires extremely high intensities.

The ultrasound tagging of light is disclosed also in the following publications: U.S. Pat. Nos. 5,174,298; 5,286,968; 5,212,667; 5,951,481; 6,041,248; WO 95/33987; Fay A. Marks et al, "*Comprehensive approach to breast cancer detection using light: photon localization by ultrasound modulation and tissue characterization by spectral discrimination*", SPIE, vol. 1888, pp. 500–509; and G. D. Mahan et al., "*Ultrasonic tagging of light: theory*", Proc. Natl. Acad. Sci. USA, 95, 14015, (1998).

U.S. Pat. No. 5,286,968 discloses a technique of multi-channel analog signal detection, aimed at obtaining synchronous detection with a CCD camera. This technique is based on a fast laser modulation.

U.S. Pat. No. 5,212,667 discloses a technique of light imaging in a scattering medium using ultrasound probing and speckle image differencing. According to this technique, coherent laser light impinges onto a scattering medium, disposed between two parallel surfaces, in a direction perpendicular to said surfaces. Light emerging from the medium is a superposition of a multitude of scattered wavelets, each representing a specific scattering part. These wavelets are projected onto the viewing plane of a two-dimensional photodetector array, where they interfere with each other, giving rise to a speckle pattern. Ultrasound pulses propagate into the scattering medium in a direction substantially parallel to said surfaces, and are focused onto the probed region, thereby effecting changes in the position of the scatterers and causing a change in the speckle pattern. This method, however, based as it is on a unidirectional laser beam, has a limited capability of providing information on the scattering medium.

U.S. Pat. No. 5,951,481 discloses a technique for non-invasive measurement of a substance using ultrasound for modulating light that is back-scattered from the region of interest. Here, pulsed ultrasound and a doublet of light pulses are used, and the detected light is not a diffuse light, but a back-scattered, quasi-ballistic light.

U.S. Pat. No. 6,041,248 discloses a technique for frequency encoded ultrasound modulated optical tomography of dense turbid media. This technique utilizes frequency chirped ultrasound and modulated photomultiplier.

SUMMARY OF THE INVENTION

There is accordingly a need in the art to facilitate two- or three-dimensional mapping of a region of interest in a scattering medium by providing a novel method and apparatus based on the principle of interaction of diffused light (light that experienced a large number of scattering events in a medium) with ultrasound radiation.

The present invention provides for real-time analysis of data indicative of the detected diffused light affected by said interaction to enable real-time imaging (less than a few seconds per image) and monitoring of a region of interest in the medium (e.g., a blood volume), and/or oxygen saturation, as well as other light absorbing agents within the medium. This technique is based on time and spatial multiplexing of light by a plurality of ultrasound waves at differently located sample volumes (points) in a medium, as well as proper fast signal processing.

The main idea of the present invention consists of providing an acousto-optic interaction between electromagnetic waves (e.g., laser light) and ultrasound pulses in order to localize absorption in a turbid medium (tissues), and affecting the phase of either one of the light or ultrasound signals, or both. By providing a certain phase relationship between ultrasound pulses and/or light signals (the so-called "phase coding"), the location of interactions along the axis of propagation of the ultrasound beam (Z-axis) can be provided. In order to locate these interactions in the X-Y plane, the ultrasound beams are directed from a plurality of locations in the X-Y plane. By this, a two or three-dimensional image of a region of interest can be obtained. The ultrasound pulses used in the technique of the present invention are sinusoidal pulses of several (at least one) cycles. An example of such pulses is the Doppler mode used in medical ultrasonography. These Doppler mode pulses are different from doublet pulses that are typically used for echography.

The transmission of ultrasound beams to different locations in the X-Y plane can be implemented by using one or more ultrasound transducers (each operable to periodically transmit ultrasound pulses with a certain phase delay). If a single transducer is used, the X-Y plane is scanned by displacing the transducer. When using a plurality (one- or two-dimensional array) of transducers operating in parallel, each transducer transmitting ultrasound pulses of a frequency slightly different from that of the other transducers, a power spectrum of the temporal trace automatically gives the signal of all frequencies. It is therefore possible to translate the signal in the frequency domain into the transducer's position in the X-Y plane.

Alternatively, a phase-array of ultrasonic transducers, similar to those typically used in ultrasonic medical imaging, can be used in order to provide the spatial frequency and phase coding. To this end, the electrical signal that is sent to each transducer of the phase-array comprises several frequencies, and phase delays are chosen appropriately for each frequency.

In order to allow identification of the interaction between the electromagnetic and ultrasound radiation components that occur at different locations along the Z-axis, the certain phase relationship between the ultrasound pulses may be obtained by providing different phases of successive ultrasound pulses. Preferably, in order to obtain a sufficient signal-to-noise ratio (SNR) in the detected signal, different phases of the ultrasound pulses are such that each pulse presents a different part of a common sinusoidal signal. Alternatively, ultrasonic pulses with an identical temporal profile may be generated, while the laser intensity is modulated.

There is thus provided according to one aspect of the present invention, a method of detecting the effect of interactions of electromagnetic radiation with ultrasound radiation at different locations within a region of interest in a scattering medium to thereby enable imaging of said medium, the method comprising the steps of:

(i) generating a plurality of sequences of ultrasound pulses, each comprising at least one sinusoidal cycle;

(ii) generating incident electromagnetic radiation of at least one wavelength;

(iii) directing the plurality of sequences of said pulses of ultrasound radiation towards a plurality of locations, respectively, in said region of interest within an X-Y plane perpendicular to axes of propagation of the ultrasound pulses, while illuminating said region of interest with the incident electromagnetic radiation, and controlling phases of either the ultrasound radiation pulses or the electromagnetic radiation components, to thereby produce signals of the electromagnetic radiation, each being a frequency modulated by a frequency of the ultrasound radiation and allowing identification of said interactions that occur at said plurality of locations in the X-Y plane and in a plurality of location along the Z-axis, and;

(iv) detecting the modulated signals of the electromagnetic radiation and generating data indicative thereof, the analysis of said data enabling the imaging of the region of interest.

By appropriately analyzing the detected signals, information on absorbing substances in the region of the medium can be obtained.

According to another aspect of the present invention, there is provided an apparatus for detecting an effect of interactions of electromagnetic radiation with ultrasound radiation pulses at different locations within a region of interest in a scattering medium to thereby enable imaging of said medium, the apparatus comprising:

(a) an ultrasound firing unit comprising a transducer arrangement operable to transmit a plurality of sequences of said pulses of ultrasound radiation to a plurality of locations in said region of interest with an X-Y plane perpendicular to the axes of propagation of the ultrasound pulses; and an electromagnetic radiation source operable to illuminate said region of interest with incident electromagnetic radiation of at least one wavelength, to thereby produce signals of the electromagnetic radiation, each being a frequency modulated by a frequency of the ultrasound radiation and allowing identification of said interactions that occur at said plurality of locations in the X-Y plane and;

(b) a phase control utility associated either with the ultrasound firing unit or with the electromagnetic radiation source, and operable to affect either phases of the ultrasound radiation pulses or phases of the electromagnetic radiation components, to thereby allow identification of said interactions that occur at different locations along the Z-axis;

(c) a detector unit for detecting said modulated signals and generating data indicative thereof; and (d) a control unit for operating said ultrasound firing unit, said electromagnetic radiation source, and said phase control utility, the control unit comprising a data processing and analyzing utility for analyzing the data generated by the detector to enable said imaging.

The technique of the present invention provides for obtaining a functional image of the region when utilizing the combination of electromagnetic and ultrasound radiation. It should be understood that by means of ultrasound radiation only (i.e., by operating the ultrasound firing unit and a suitable detector), a structural image of the region of interest can be obtained. Hence, by selectively operating the ultrasound firing unit and the electromagnetic radiation source with corresponding detectors, both the functional and structural image can be obtained and registered with each other.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 15B illustrates the profile (pulse envelopes) of the phase array transducer operating with three frequencies;

DETAILED DESCRIPTION OF THE INVENTION

Figure 1A:
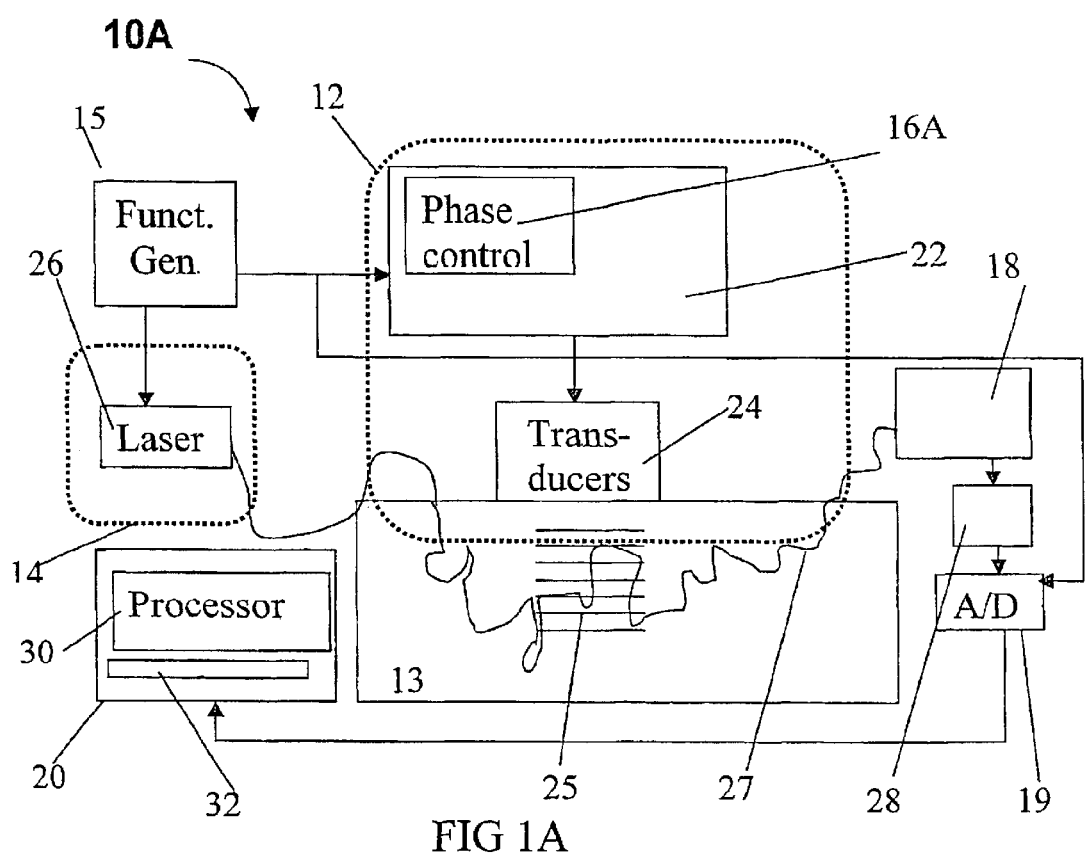
FIGS. 1A and 1B are schematic illustrations of apparatuses according to the invention, constructed and operated for affecting the phases of, respectively, ultrasound pulses and light components.

Referring to FIG. 1A, there is illustrated an apparatus 10A constructed and operated according to one embodiment of the present invention for ultrasound modulated light tomography. The apparatus 10 comprises such main constructional parts as an ultrasound firing unit 12 coupled to an optically turbid medium 13 to be imaged (tissues); an illuminator 14 (constituting an electromagnetic radiation source) optically coupled to the medium 13; a phase control utility 16A, which in the present example is associated with the ultrasound firing unit 12; a detector 18; and a control unit 20.

The ultrasound firing unit 12 comprises a pulse-ultrasound generator 22 (including an electronic beam forming unit, and array of amplifiers), and a transducer arrangement 24. The operation of the ultrasound firing unit 12 is aimed at delivering the proper ultrasound wave within the body.

A function generator 15 transmits a triggering signal TS to the pulsed ultrasound generator 22 and to an analog to digital converter (card) 19. Concurrently, the generator 22 transmits an electrical signal to the transducer arrangement 24 through the phase control utility 16A to thereby actuate one or more transducers to transmit, respectively, one or more ultrasound signals 25 into a region of interest in the medium. Each ultrasound signal 25 is transmitted in the form of a sequence of ultrasound pulses in a predetermined manner, as will be described more specifically further below.

The illuminator 14 comprises one or several laser devices 26 generating incident radiation of at least one wavelength (preferably in a range of 690–900 nm), which propagates towards the region of interest. Laser light is diffused (scattered) by the medium, and the diffused light 27 interacts with the ultrasound signal 25, and the signal resulting from this interaction is detected by the detector 18. The electric output of the detector 18 is directed to the analog-to-digital converter through a band-pass filter and amplifier 28, to thereby produce a corresponding digital signal (presenting measured data) received by the control unit 20. A data processing and analyzing utility 30 of the control unit applies a power spectrum operation to the measured data, and identifies variations in light intensity at different frequencies to determine the location and nature of objects in the turbid medium. Measurement results are then presented on a display 32.

Figure 1B:
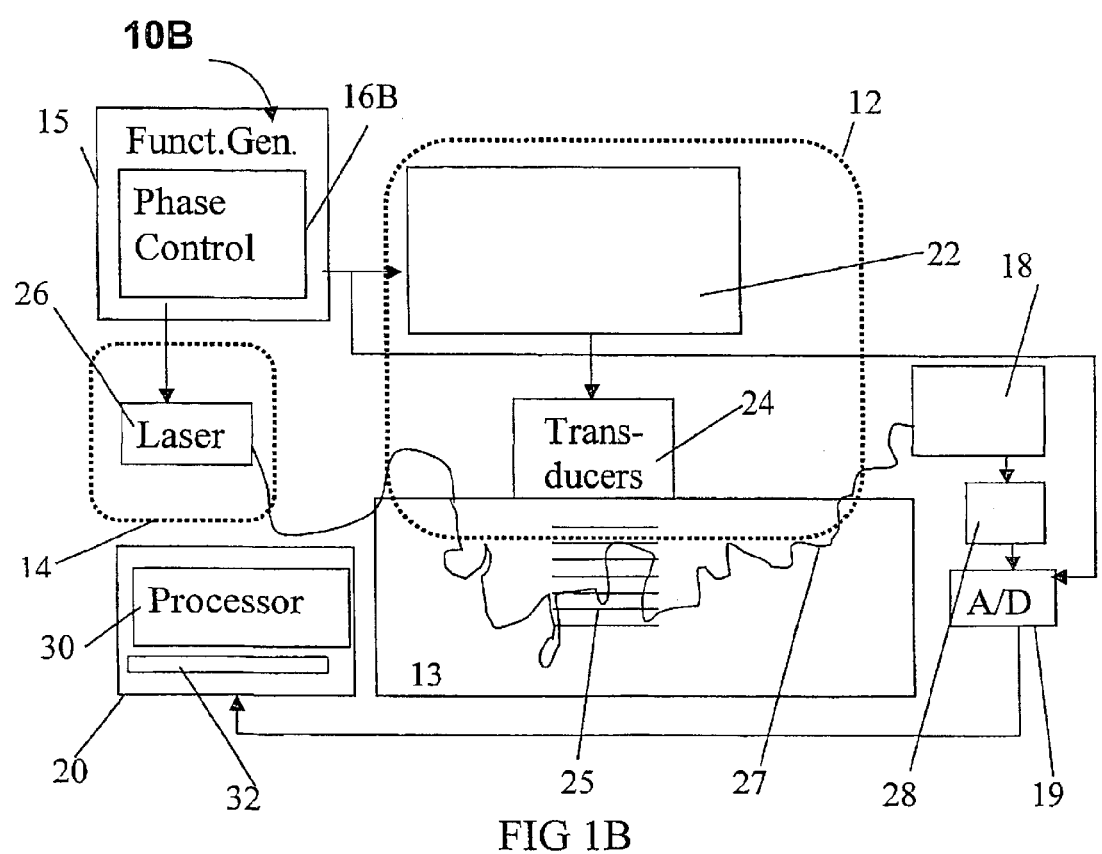

FIG. 1B illustrates an apparatus 10B for ultrasound modulated light tomography constructed and operated according to another embodiment of the present invention. To facilitate understanding, the same reference numbers are used to identify the components that are common in the examples of FIGS. 1A and 1B. Here, a phase control utility 16B is associated with the illuminator 14, and is a part of the function generator 15. The principles of the operation of apparatus 10B will be described more specifically further below with reference to FIG. 19.

The interaction between the light wave and the ultrasound results in that the frequency of light is shifted by the frequency of the ultrasound, and the amount of absorbing agent can be determined from the change in the absorption obtained at the frequency shifted light signal. The light source, the probed region, and the detector do not have to be specifically aligned with each other, and can have any geometric configuration, provided that enough photons reach the detector. This allows multiple-source/detector configurations, with the increase in the signal to noise ratio and better light filling of the tissues.

The interaction is as follows: The light source emits light of frequency $\omega$ into the probed region (region of interest). The ultrasound pulses of frequency $\Omega_{US}$ are transmitted into the probed region. The current location(s) of the interaction in the X-Y plane is defined by the current location of the transducer(s). The ultrasound modulated light having a shifted frequency $\omega+\Omega_{US}$, and non-modulated light having the frequency $\omega$ are received by the detector, which mixes them and generates a signal modulated at the ultrasound frequency. Hereinafter, the expression "modulated signal" will mean the signal detected by the detector and representing the intensity of the ultrasound modulated light (as a result from said interaction), and the expression "non-modulated signal" will mean the signal detected by the detector and representing the intensity of the light not modulated by the ultrasound (having no interaction with the ultrasound signal). The word "signal" without specification will refer to both the modulated and the non-modulated signal.

Light propagating through the medium (patient's body) experiences the absorption throughout the regions in the medium. If the ultrasound wave is located in the region of the medium, and the frequency of the light is changed, detector(s) outside the medium can detect light that has passed through the medium and selectively detect the ultrasound-modulated light. The ratio between the modulated signal and the non-modulated signal is mainly determined by the local absorption changes. Non-modulated light originating from the probed region is detected together with the modulated light. This is highly desirable in order to remove the influence of global changes in the probed region.

The change in the absorption of said ultrasound modulated light in the probed region, due, for example, to changes in the oxygenation state of the hemoglobin, is represented by an analog signal, that can then be transformed to a digital signal, be processed, and, if desired, visualized. The modulated signal is proportional to the amplitude of the light field passing through the probed region, from which the absorption is calculated: the changes in the modulated signal reflect changes of the intensity of the light passing through the probed region, which, in turn, reflects changes in the absorption in the probed region. The signal can be processed using an analog-to-digital card with a sampling cycle, which is high enough to sample effectively the signal at the ultrasound frequency, the digitized signal being transferred to a memory and then processed using power spectrum techniques, which directly gives the signal at the ultrasound frequency. By averaging the signal at several frequencies nearby the ultrasound frequency, the average background noise can be obtained and is then subtracted from the signal at the ultrasound frequency.

As described above, the basic idea is to use acousto-optic interaction between laser light and ultrasound in order to localize absorption in the turbid medium. The signal that is detected is a coherent mixing of ultrasound modulated (USM) and not-modulated light. This means that the laser coherence length must be long enough. A good number is between 10 cm and 3 m (path length of the photons in the tissues). The laser coherence causes the creation of speckle light, which is a characteristic of laser light undergoing a diffusive process caused by the interference between different wavelets originating from the same laser source. The signal is embedded within the speckle.

It is known that in order to obtain a good signal to noise ratio (SNR), the number of speckles "seen" by the detector should be reduced (M. Kempe et al., "*Acousto-optic tomography with multiply scattered light*", J. Opt. Soc. Am. A, 14, 5, 1151, (1997)). The speckle decorrelation time $\tau_{speckle}$ is the typical time at which the speckle is moving, or, more precisely, the time at which there is a change in the relative phases of the interfering wavelets. If $\tau_{speckle}$ were infinite, the modulated signal (light signal interacted with the ultrasound signal) would be an infinitely long sinusoidal signal without any phase and amplitude disruption. However, if this time $\tau_{speckle}$ is finite, which is the practical case in living tissues, then the modulated signal presents phase (and amplitude) disruptions every $\tau_{speckle}$ on average. The signal at the ultrasound frequency increases linearly with the data acquisition duration $\tau_{acq}$ until $\tau_{acq}$ is approximately equal to $\tau_{speckle}$. Then, this ultrasound signal grows only like the square root of the ratio $\tau_{acq}/\tau_{speckle}$. Since the noise also grows as the square root of the signal, it means that, data acquisition durations longer than $\tau_{speckle}$ do not increase the signal to noise ratio. In practice, the optimum trace duration $\tau_0$ can be up to two or three times the speckle decorrelation time.

As indicated above, the ultrasound signal 25 is a sequence of pulses, where each pulse is a sinusoidal pulse composed of several cycles. This means that a small number of periods (between one and a few tens, depending on the application and frequency) are transmitted, followed by a longer period of silence.

In order to obtain two-dimensional pictures of the region of interest (of the absorbing agent existing therein), it is necessary to locate the ultrasound in different zones of the X-Y plane of the probed region. This can be done in the following different ways:

(1) using a single transducer and scanning the X-Y plane in the region of interest with the ultrasound signal generated by this transducer, (2) using a one-dimensional array of transducers aligned along the X-axis, operating the transducers to simultaneously transmit ultrasound signals of different frequencies, and scanning the X-Y plane with this array of transducers; and (3) using a two-dimensional array of transducers and operating the transducers to simultaneously transmit ultrasound signals of different frequencies.

The scanning can be performed either by displacing the transducers with respect to the medium, or by using a system of phase-array transducers, where the scanning is performed by electronic means only (namely, changing the direction of the ultrasound wave).

In order to obtain in-depth imaging, the interaction zones should be provided at different locations along the Z-axis, i.e., the axis of propagation of the ultrasound wave. This can be implemented by using ultrasound pulses.

During the pulse to pulse duration, the ultrasound pulse travels a certain distance, and a unique relationship exists between the specific pulse' position inside the medium and the time it spent to reach this position. By controlling the delay between the time at which the ultrasound transducer emits the ultrasonic pulse and the time at which the pulse reaches the region of interest, it is possible to control longitudinal coordinates (along the Z-axis) of the location of the ultrasound pulse. For each delay, there is one specific position in the Z-direction (the probed depth z). The probed depth z is given by the propagation of the pulse of duration $\tau_p$ inside the tissues. If $v_s$ is the speed of sound in the tissues, then the pulse repetition frequency (i.e., the inverse of the time interval between two successive pulses) is given by $PRF=v_s/z_{max}$, where $z_{max}$ is the maximum depth desired. This distance can be divided into $n_z$ regions in which the ultrasound pulse spends a time $\tau_b$. If the transducer is operated such that 1/PRF is smaller than the optimum trace duration $\tau_0$, then there is no phase disruption in average during a period of several pulse firings, and the signal at the detector is continuous during several pulse-to-pulse periods. The effective cumulated time spent by the successive ultrasound pulses in one of the $n_z$ regions during the time $\tau_0$ is $\tau_{eff}=\tau_0/n_z$. The cumulated signal at the detector corresponding to a given region is formed of $n_b$ blocks of duration $\tau_b$, wherein $n_b=\tau_{eff}/\tau_b$. This corresponds to a signal (after power spectrum processing) of bandwidth $\delta f \sim n_z/\tau_0$. However, this bandwidth can be achieved only if the cumulated signal at the detector is a sinusoid with no phase jump. To this end, the phase control utility is operated to provide a time delay and a specific phase relationship between successive ultrasound pulses in the sequence.

According to one embodiment of the invention, scanning along the Z-axis utilizes a fast detector: its response time is at least twice the highest operated ultrasound frequency. In this specific embodiment, the laser is not modulated and the ultrasound pulse sequence to be generated by the ultrasound firing unit is programmed in a specific manner, as will be described below. This technique is aimed at providing maximum SNR and concentrating the signal in the narrowest frequency peak (or peaks) centered at the ultrasound frequency (or frequencies).

This is done by artificially creating a long time series of collected data (detected signals) for each location along the propagation axis (Z-axis). In order to do so, all the data acquired when the successive ultrasound pulses pass through a given location are concatenated. This time series of data is called a trace. By doing this, several long sinusoidal traces are obtained at a given frequency, whose power spectrum shows a narrow peak centered at the ultrasound frequency. Each such trace corresponds to a given location along the Z-axis.

Figure 2:
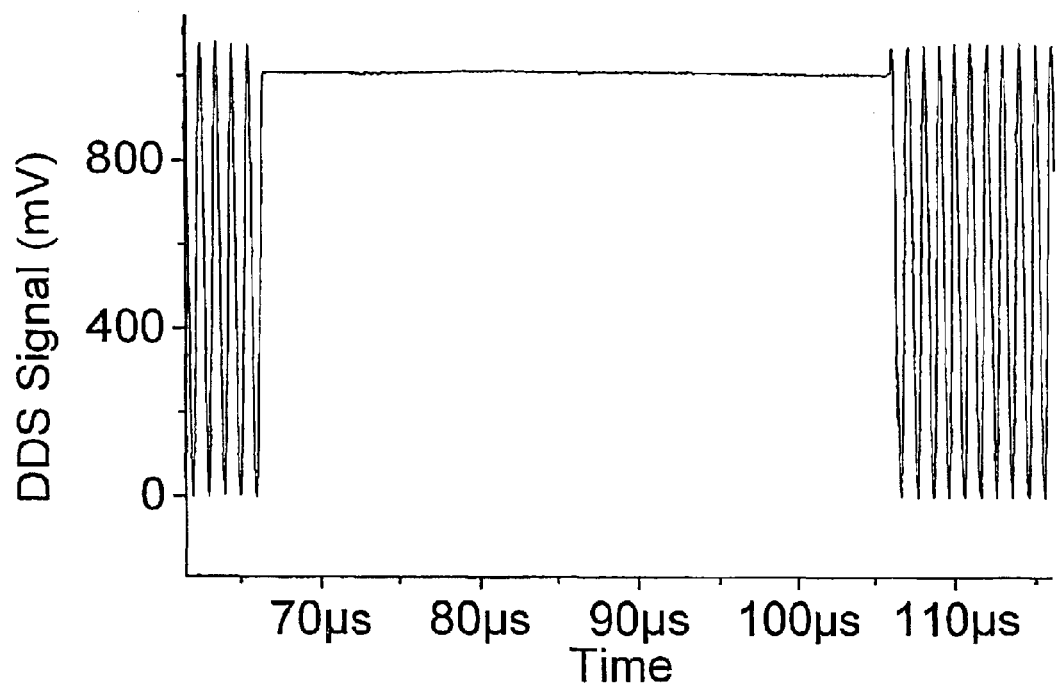
FIG. 2 illustrates an ultrasound pulse sequence (continuous trace) suitable to be used in the present invention, the trace being obtained by using a DDS (Direct Digital Synthesizer) chip aimed at obtaining the proper signal generation.

It is important to note that the phase continuity should be kept. As shown in FIG. 2, this is realized by ensuring that for every series of ultrasonic pulses, each pulse beginning phase is the same as the preceding pulse ending phase.

Figure 3:
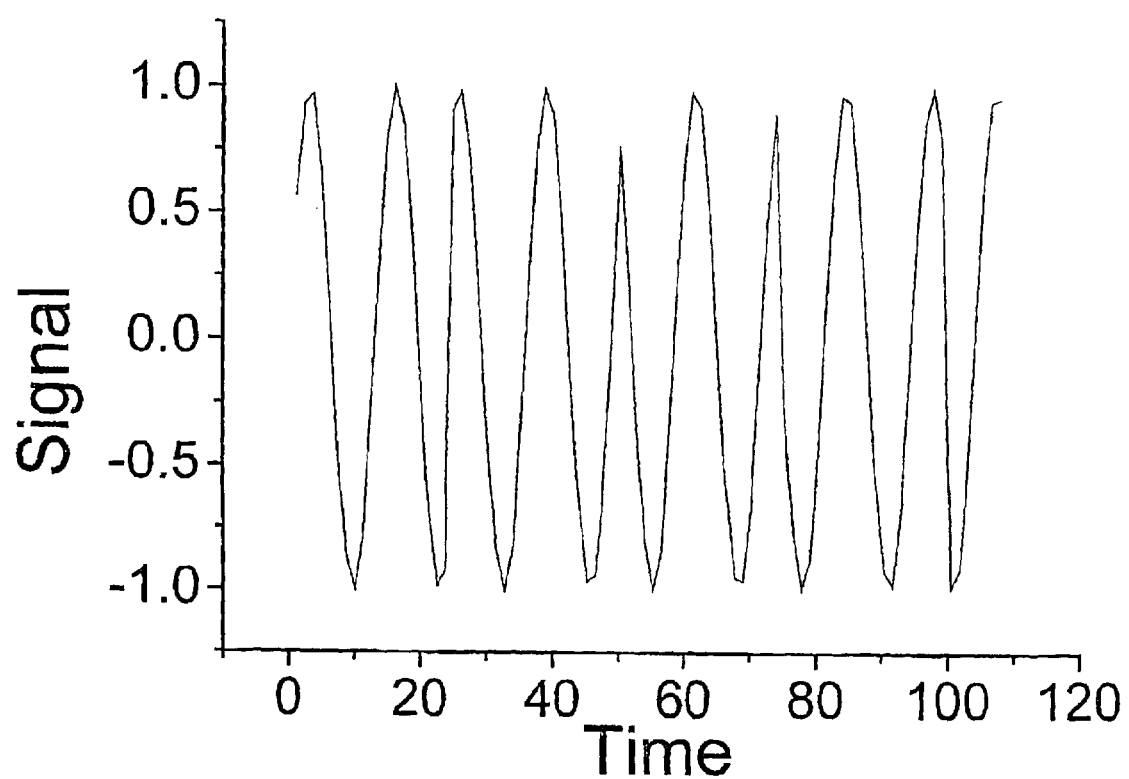
FIG. 3 illustrates a sinusoidal trace comprising discontinuities.

The disadvantages of using a sinusoidal trace comprising discontinuities will now be described with reference to FIGS. 3, 4A–4B and 5A–5B. FIG. 3 illustrates the sinusoidal trace comprising phase discontinuities. The power spectrum of such trace obtained by Fourier transformation has a peak centered at the sinusoidal frequency, but with a very large width (and possibly some lateral lobes) and much smaller amplitude (since the energy is spread over a relatively large frequency range). As a result, the number of frequencies that can be included within a given frequency range without cross-talk is much smaller, as compared to the case of phase continuity.

Figure 4A:
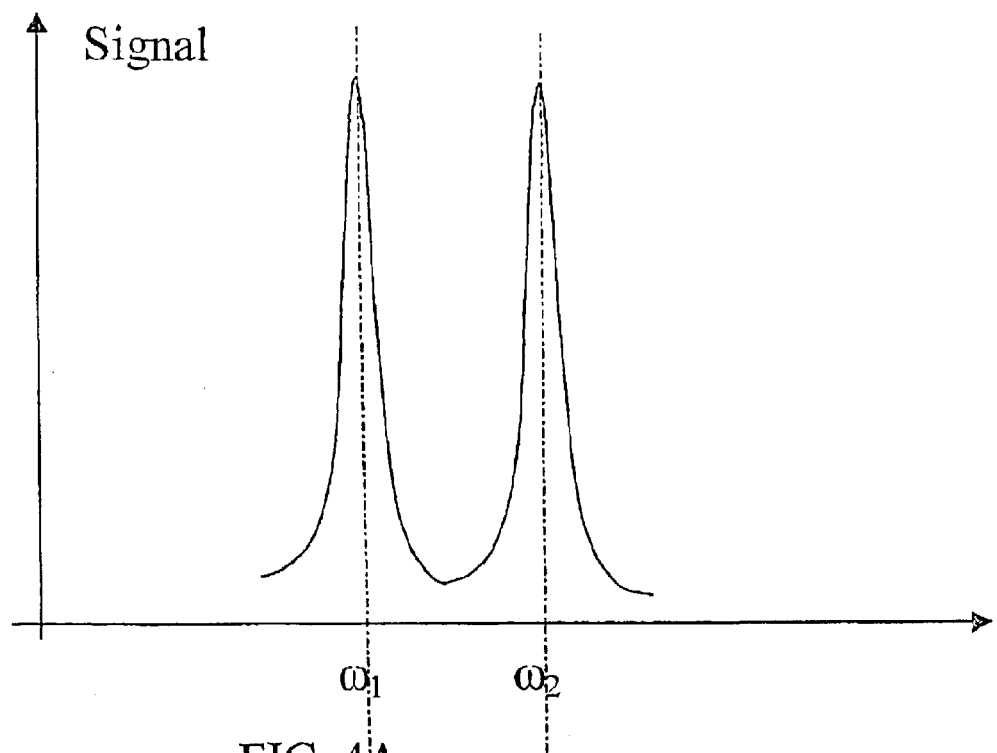
FIGS. 4A and 4B illustrate the power spectra corresponding, respectively, to a continuous sinusoidal trace, and to a sinusoidal trace with phase discontinuities.
Figure 4B:
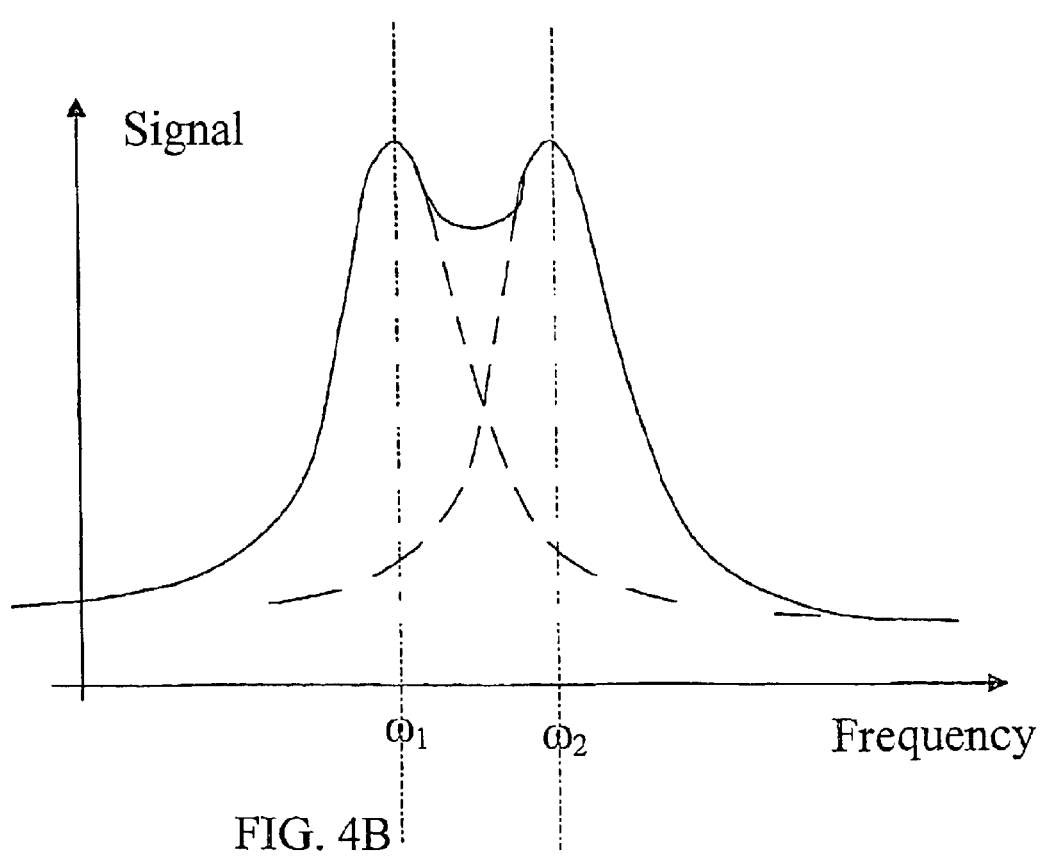

FIGS. 4A and 4B illustrate the power spectra corresponding, respectively, to the trace in the form of a continuous sinusoid, and to the trace with phase discontinuity. In the example of FIG. 4A, two peaks at two operating frequencies $\omega_1$ and $\omega_2$ are completely timely separated. In the example of FIG. 4B, the two peaks at the two operating frequencies $\omega_1$ and $\omega_2$ are crossed, and the part of the signal (shown in dashed lines) is lost due to the cross-talk.

Figure 5A:
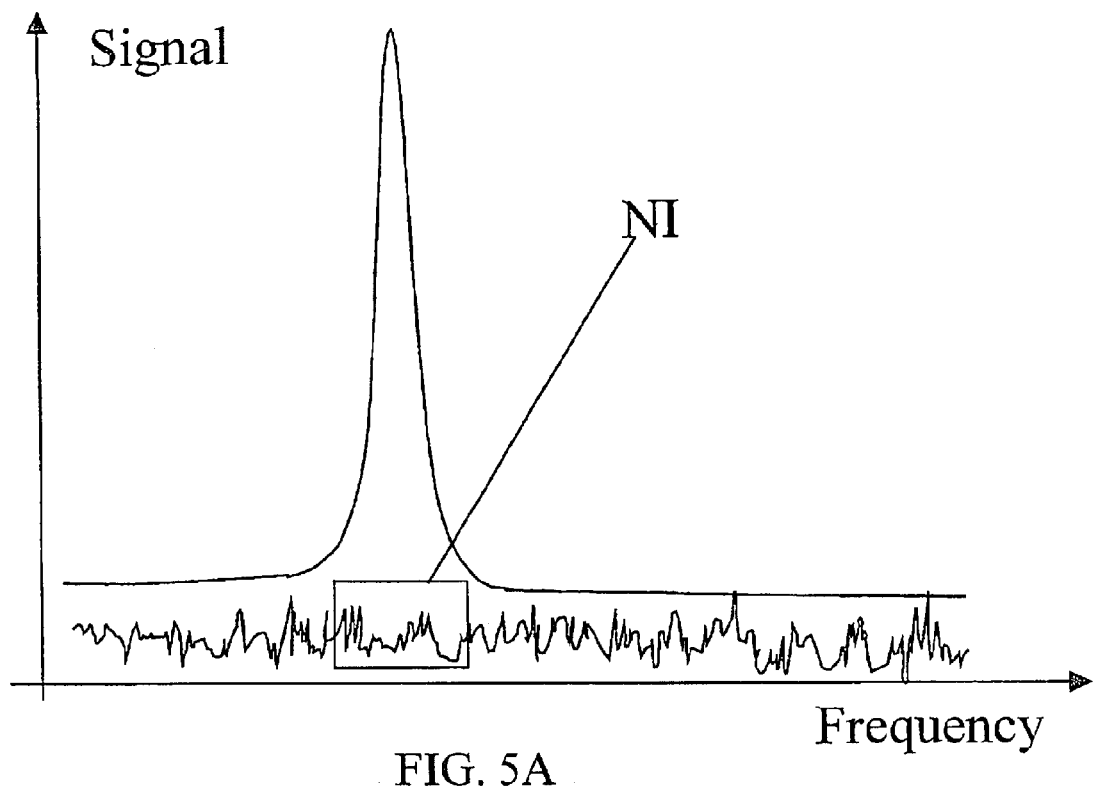
FIGS. 5A and 5B illustrate the power spectrum with the noise integration over the frequency range where the intensity peaks take place for, respectively, the case of the continuous sinusoidal excitation, and the case of phase discontinuities.
Figure 5B:
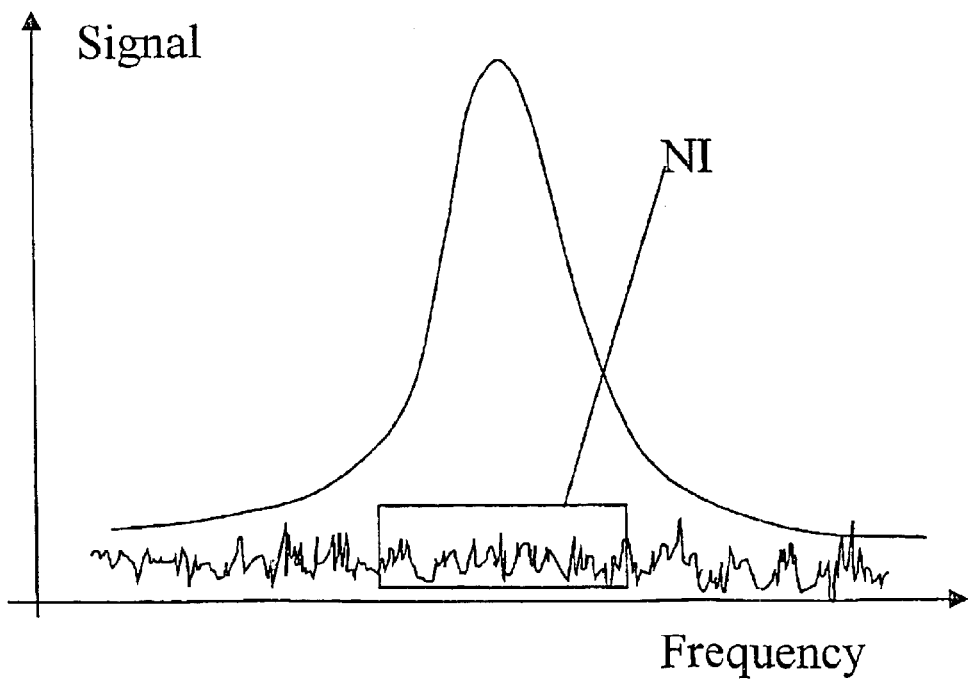

Additionally, since the signal must be integrated over a large frequency range, the noise is also integrated over a large frequency range, and therefore the signal to noise ratio decreases approximately linearly with the frequency span. FIGS. 5A and 5B illustrate the power spectrum with the noise integration NI over the frequency range where the intensity peaks take place for, respectively, the case of a continuous sinusoidal excitation (noise integration over a small frequency range), and the case of phase discontinuities (noise integration over a large frequency range).

Hence, in order to keep the phase continuity by ensuring that for every series of ultrasonic pulses, each pulse beginning phase is the same as the preceding pulse ending phase (FIG. 2), the process is as follows:

The ultrasound pulses are generated at a given repetition rate frequency, such that each pulse beginning phase is the same as the preceding pulse ending phase. The ultrasound pulse and the continuous wave laser light propagate within the medium and the interactions between them occurs. The light signals resulting from the interactions are located outside the medium using one or several fast detectors. Analog data indicative of the detected light is transformed into digital data using the analog to digital converter (19 in FIGS. 1A and 1B). Data indicative of the corresponding location of the ultrasonic pulse (location of interaction) is identified. For each location along the ultrasound pulse propagation axis (Z-axis), traces of data are created, by concatenating successive data corresponding to the ultrasonic pulse location. A power spectrum operation is performed on each of the so-obtained traces, and the background-free peaks' amplitudes are calculated for each of the different peaks and for each location. These data are further processed and the results are displayed.

Figure 6A:
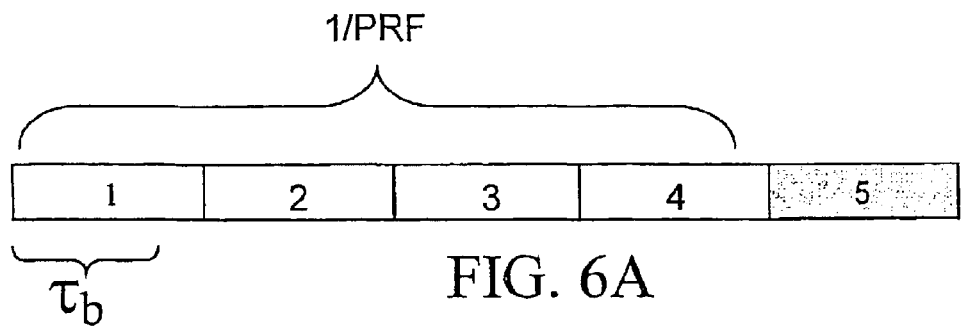
FIGS. 6A to 6D illustrate the scheme of the ultrasound pulse firing and the logical process of the reshaping procedure, according to the invention.
Figure 6B:
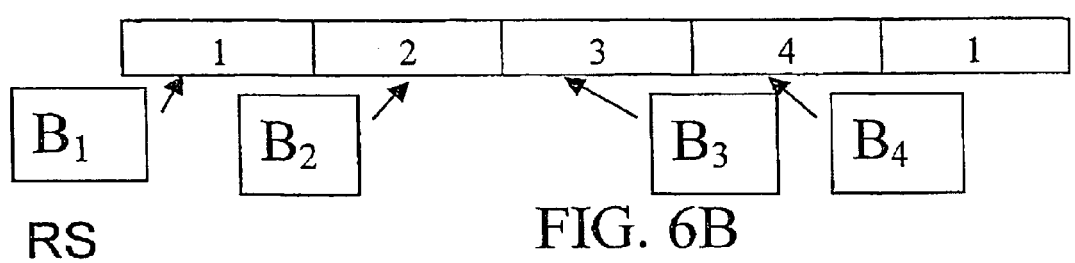
Figure 6C:
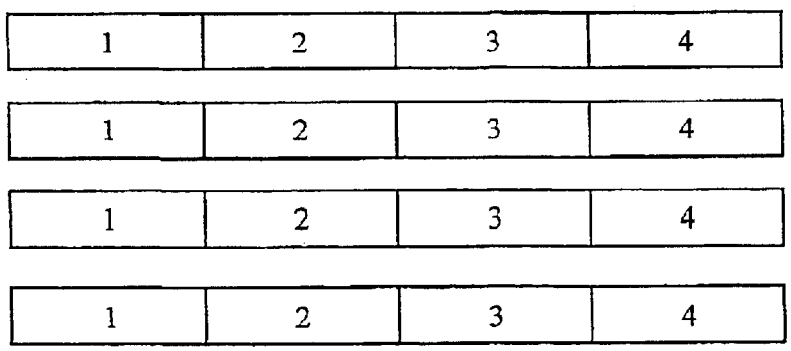

The scheme of the ultrasound pulse firing, and the logical process of the reshaping procedure (performed by the control unit) will now be described with reference to FIGS. 6A–6D. As shown in FIG. 6A, the pulse is launched into the medium and continuously interacts with photons that are received by the detector. This interaction occurs for each of the $n_z$ locations during a period $\tau_b$. Since the speed of light propagation is much higher than that of sound, the light propagation time is negligible. At each relative time from the ultrasonic pulse firing, such an interaction occurs at a specific position along the ultrasound beam propagation axis (Z-axis). After a time period of 1/PRF, a further (new) pulse $P_2$ is launched, and so on. The pulse is at the same location in the medium every 1/PRF time. Since the process is cyclic, it is possible to construct several traces from the acquired data. Each trace corresponds to a given position along the Z-axis and is obtained by appending the signals of length $\tau_b$ appearing every 1/PRF. FIG. 6B symbolically represents the signal RS that is received from the detector. Each individual block from blocks $B_1$–$B_4$ corresponds to the signal coming from the corresponding one of $n_z$ regions ($n_z$=4 in the present example) during the duration $\tau_b$.

Figure 6D:
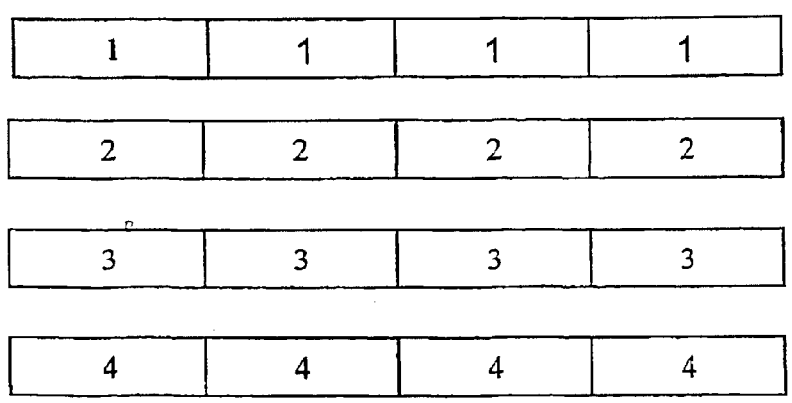

After digitization, the signal is cut into a series of small data series corresponding to a duration 1/PRF, and starting at the time when the successive ultrasonic pulses are fired. Different rows in FIG. 6C correspond to the different pulse firings. Obviously, the first block of each row is related to the same position of the ultrasound pulse inside the medium. FIG. 6D illustrates the fabrication of the different traces corresponding to the different locations performed by concatenating the different columns obtained in FIG. 6C.

A critical aspect of this embodiment is that the apparatus is operated so as to ensure that when the blocks are appended, there is no phase jump. As indicated above with reference to FIG. 2, this is realized by ensuring that for every series of ultrasonic pulses, each pulse beginning phase is the same as the preceding pulse ending phase. There are several ways of implementing the same.

One way is to send the waveform directly from the programmable function generator. Another way is to use Direct Digital Synthesis DDS technology, according to which a sinusoidal waveform is stored in a look-up table (LUT) as a vector of numbers (usually with high precision). An internal or external TTL clock is sent to the chip. At each clock tick, the chip takes a number from the LUT and sends it to a Digital to Analog (D/A) module that transforms the number into a very precise voltage.

The clock signal is sent for a period $\tau_b$ to the DDS, which produces a sinusoidal signal during this time period. Then, the clock is stopped for a time period of 1/PRF-$\tau_b$, during which the DDS does not send any signal to the D/A module. Thereafter, the clock again sends a signal to the DDS, which starts at the position at which it was stopped. The phase of the ultrasound is therefore kept as needed.

Construction may be such that each transducer has its own clock. Alternatively, a common clock for all the transducers and one DDS chip per transducer can be used. In this case, each DDS delivers a different frequency using the same clock. The advantage of this construction is that all the DDS are automatically synchronized.

The signal from the DDS is sent to the amplifier that matches the transducers' needs. The amplifier has a fast enough rise time (typically ten times shorter than the inverse of the transducer's frequency). For example, the amplifier model A078 commercially available from LCF Enterprises Ltd. can be used. The amplified signal is sent to the transducer.

As indicated above, in order to localize the ultrasound beam in the X-Y plane (parallel to the surface of the transducer arrangement by which it is applied to the medium), a two-dimensional array of an ultrasound beam may be provided, e.g., by using $n_x$ time moments of beam transmission by $n_y$ transducers. Each transducer has its own frequency. Each frequency corresponds to a position on the X-Y plane. For a total excitability bandwidth $\Delta f$ of the ultrasound transducer, the maximum total number of transducers is $\Delta f/\delta f$, wherein $\delta f$ is the signal peak linewidth for each frequency. For example, if each ultrasound transducer is of the kind capable of generating pulses with frequencies in the range 1–1.5 MHz, then its bandwidth is $\Delta f$=500 kHz. If the signal peak linewidth $\delta f$ for each frequency is about 1 kHz, then the maximum possible number of transducers operating simultaneously, each at a different frequency, is 500. Because of the cross-talk effects between the transducers, it is better to choose a smaller number of transducers, e.g., a maximum value of $n_{max}=\Delta f/4\delta f$.

Since a power spectrum operation is performed, all the ultrasound signals will appear as individual peaks at their respective frequencies. For example, if 16 transducers are working in parallel, 16 different peaks will be present in the power spectrum. Therefore, the processing time and the signal to noise ratio are not dependent on the number of transducers. Since the peaks' positions are known, special Fourier transform techniques can be used, e.g., the so-called zoom Fourier transforms, chirp Fourier transforms, etc.

In order to improve the signal to noise ratio, it is necessary to average the signal obtained for a given position. This cannot be done by simply adding the temporal traces, but by adding the power spectra obtained after the power spectrum operation.

The entire process consists of the following steps: trace reshaping; power spectrum and background removal; mathematical processing for signal to noise ratio improvement; reconstruction and visualization. If real-time analysis is required, then moving average can be used or similar averaging techniques. By using frequencies where there is no ultrasound signal, the white noise background is detected and subtracted from the signal.

In order to reduce the constraints on the detectors, and to enable the use of relatively slow detectors, it is possible to modulate the laser light intensity. If the laser light is intensity modulated at a frequency $\Omega_{US}+\delta_\omega$, wherein $\Omega_{US}$ is the ultrasound frequency and $\delta_\omega$ is a frequency shift, the signal at the detector has two components: a component with the frequency $\Omega_{US}+\delta\omega$ corresponding to the original (incident) light signal, and a component with the frequency $\delta_\omega$ corresponding to the modulated signal. If, for example, $\delta_\omega$ is chosen smaller than 40 kHz, then a simple sound card, with 16 or more bits, can be used as the A/D card (19 in FIGS. 1A and 1B). Moreover, if several lasers are used, the $\delta_\omega$-shift can be chosen different for each laser, and then one single photodetector or photodetector array can be used for all the wavelengths. Direct laser modulation is in general directly available with diode lasers using a simple current modulation. In the case of several lasers modulated at frequencies $\Omega_0+\delta\omega_{wli}$ and several transducers emitting ultrasound waves at frequencies $\Omega_0 + \delta\omega_{usj}$, the signal from the $i^{th}$ wavelength and the $j^{th}$ transducer is located as the detected signal with the frequency $(\delta\omega_{usj} - \delta\omega_{wti})$.

Once the signal has been obtained in the frequency domain, the process starts again, and new traces are processed in a similar way. All the power spectra are then averaged. The signal to noise ratio grows like the square root of the number of such power spectra.

As indicated above, the ultrasound firing unit may utilize a direct array of transducers (using the phase control utility), or the known phase array transducers' arrangement.

Experiments have been conducted to obtain two-dimensional transversal and longitudinal pictures in an Agar gel, tissue-like, phantom. The Agar gel ("regular" Agar gel) was prepared by mixing 2.7% in volume of Intralipid 20% (commercially available from B. Braun Melsungen A G) with water with unclear Agar Fluka 05040 (possessing an intrinsic scattering coefficient of $\mu_s = 5$ cm$^{-1}$). The amount of 2 droplets/liter of Pelikan 4001 black ink were added in order to increase the absorption. The optical and ultrasonic properties of the gel have been matched to biological tissues.

Different cases have been examined. In the first example, the Agar sample AS was completely homogenous, without any absorber inside. In a second example (experiment), a small absorbing region was introduced, made of exactly the same Agar gel, but with the addition of carbon black (about 250 mg of carbon black per liter), called "black Agar". This was done by drilling a 9 mm-diameter hole in the Agar block, partly filling this hole with the black Agar so as to obtain a 1 cm-height, and then completely filling the hole with the regular Agar gel. This absorbing region was index matched to the surrounding medium both for the light and the ultrasound beams.

Figure 7A:
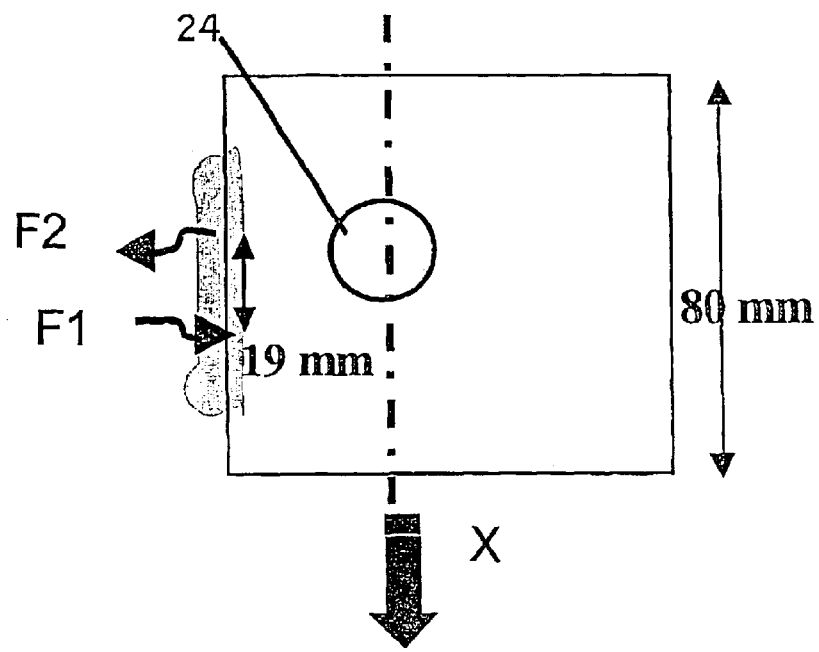
FIGS. 7A and 7B illustrate an example of the present invention, where the technique of the present invention is applied to a completely homogenous Agar sample (without any absorber inside)
Figure 7B:
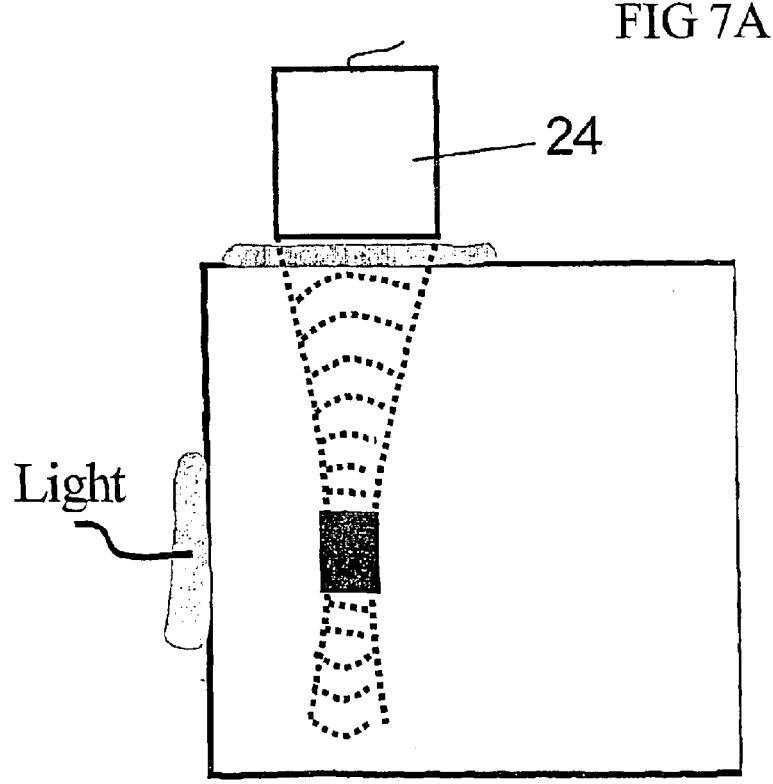

In both examples, the experimental set up shown in FIGS. 7A and 7B and the following conditions were used: The ultrasound transducer 24 was V314 model (1.5" effective diameter) commercially available from Panametrics. The laser was model S2395 (operating wavelength of 695 nm), commercially available from Melles-Griot. The detector was a fiber-coupled photomultiplier R7400U-50, commercially available from Hamamatsu. The analog to digital card was model PCI9812, commercially available from ADLink. The ultrasound wave was focused at a 1"-distance under the sample surface, and the light input and output optical fibers $F_1$ and $F_2$ were located 1.8 cm apart. The diameter of the ultrasound waist (at 6 dB) was 3 mm. The transducer 24 was physically scanned on the surface of the sample. A 14×14 matrix of transducer positions was chosen, the grid size being 3 mm. Good coupling was ensured by using an ultrasound coupling agent (Medi-pharm). At each point, measured data was obtained and power spectrum operations were performed and averaged.

As shown in the example of FIGS. 7A and 7B, the scan in the X-Z plane is performed by physically scanning the ultrasound transducer in the X-direction and by sending pulses of duration 6.4 $\mu$s to perform the scan in the Z-direction. In the specific example, the ultrasound frequency was 1.25 MHz. The scan in the X direction comprised 8 locations separated by a 5 mm-distance. The scan in the Z-direction comprised 8 locations separated by a 9.6 mm-distance. The sample was made of the regular Agar.

Figure 8:
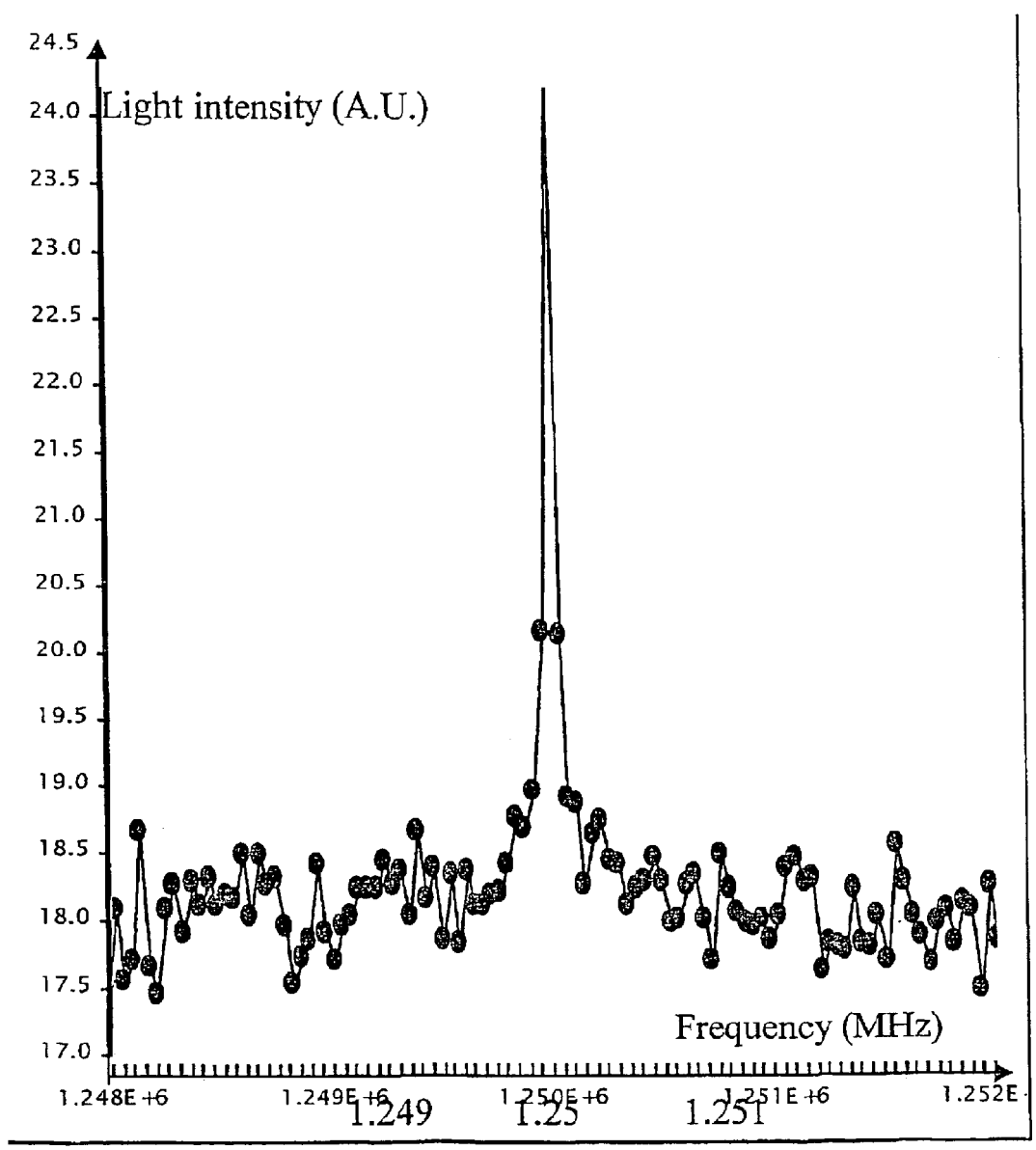
FIG. 8 illustrates an experimental power spectrum collected for each position in the X-Z plane with the example of FIGS. 7A and 7B.
Figure 9:
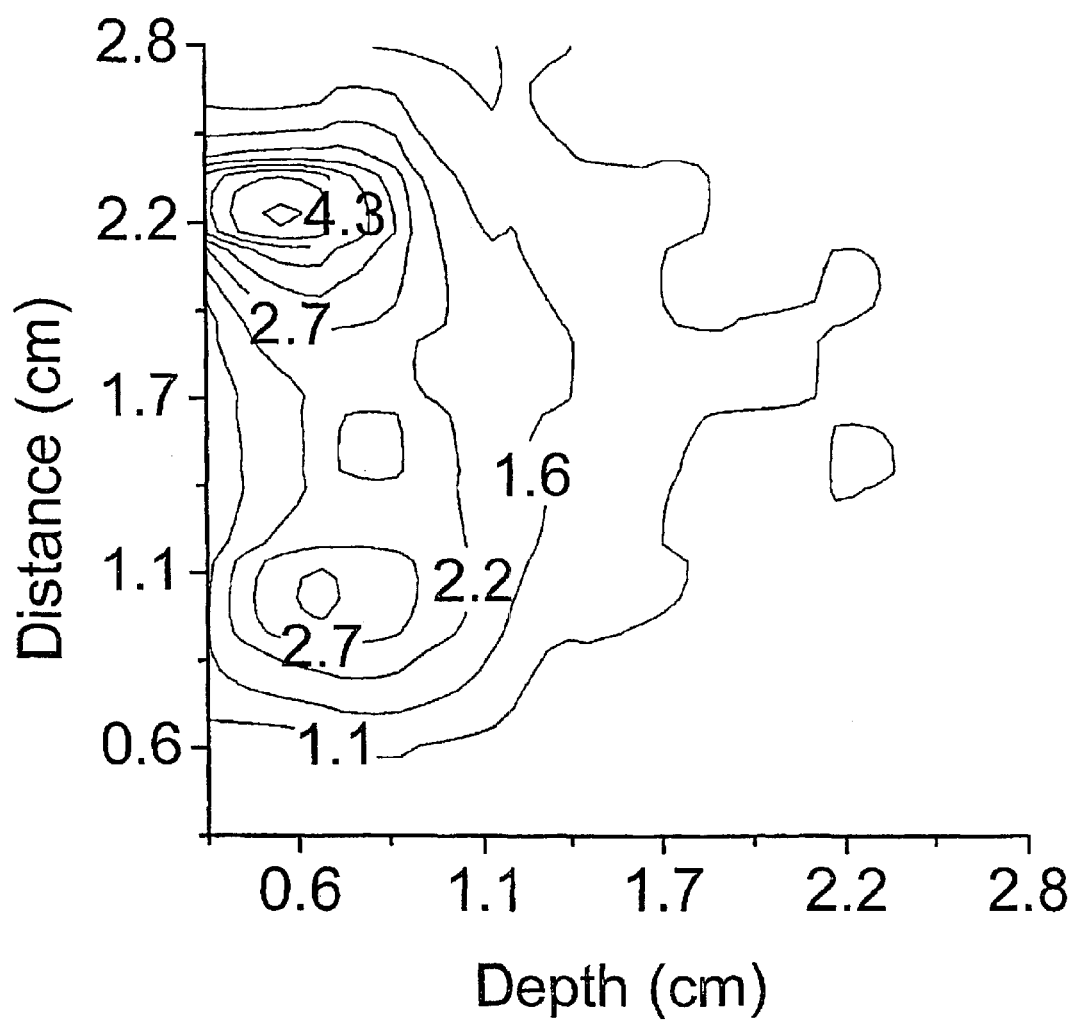
FIG. 9 illustrates the values of the power spectrum at the ultrasound frequency (after background removal) as a function of the position of the transducer, presenting a map of the absorption in the example of FIGS. 7A and 7B.
Figure 10:
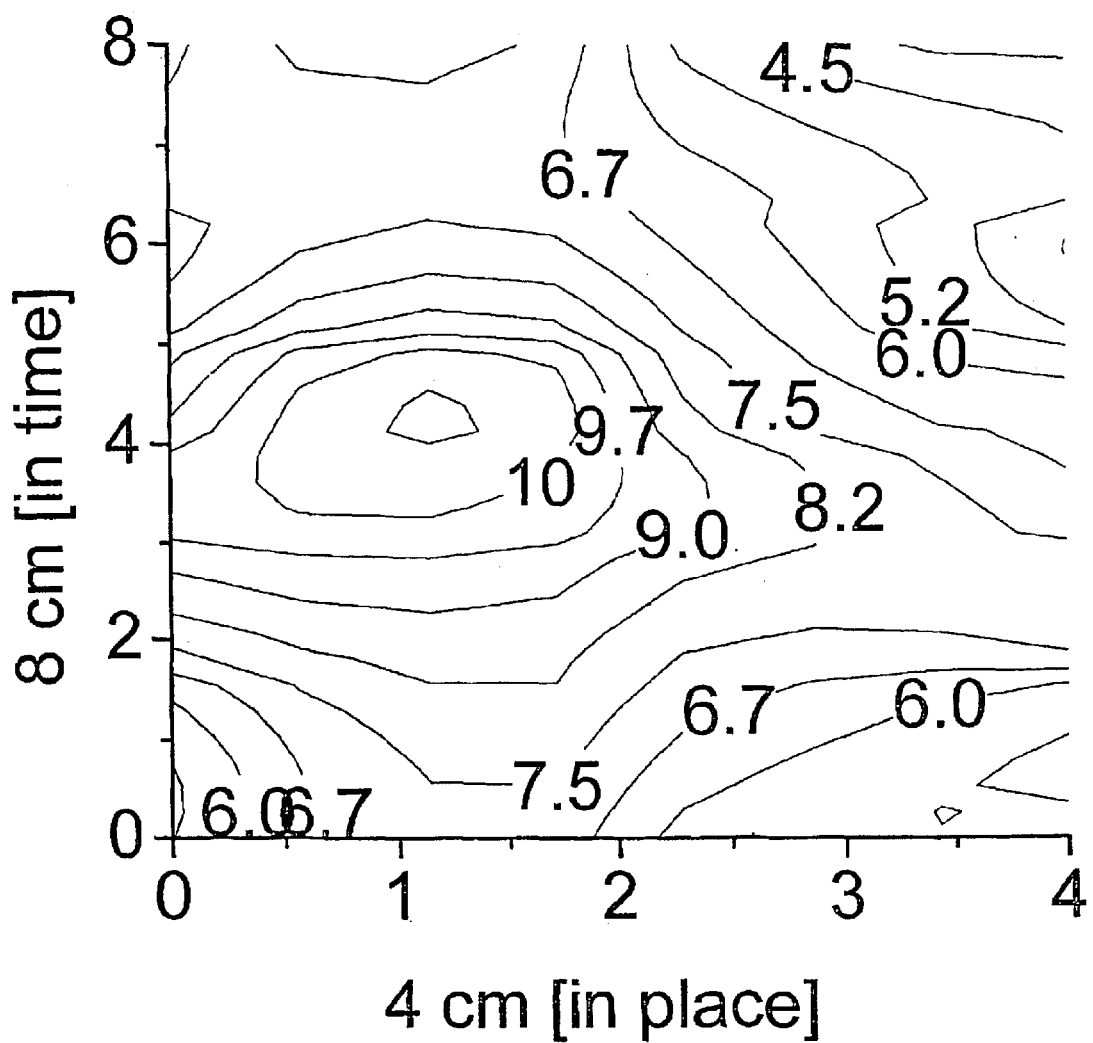
FIG. 10 illustrates the transversal picture of the photon density obtained with the technique of the present invention.

FIG. 8 illustrates a spectrum as collected for each position in the X-Z plane for the first example (completely homogenous Agar sample), and FIG. 9 illustrates the values of the power spectrum at the ultrasound frequency (after background removal) as a function of the position of the transducer, presenting a map of the absorption. This plot is in the form of a banana-shape that is typical for light transport in a diffusive media. FIG. 10 illustrates the so obtained transversal picture of the photon density.

Figure 11:
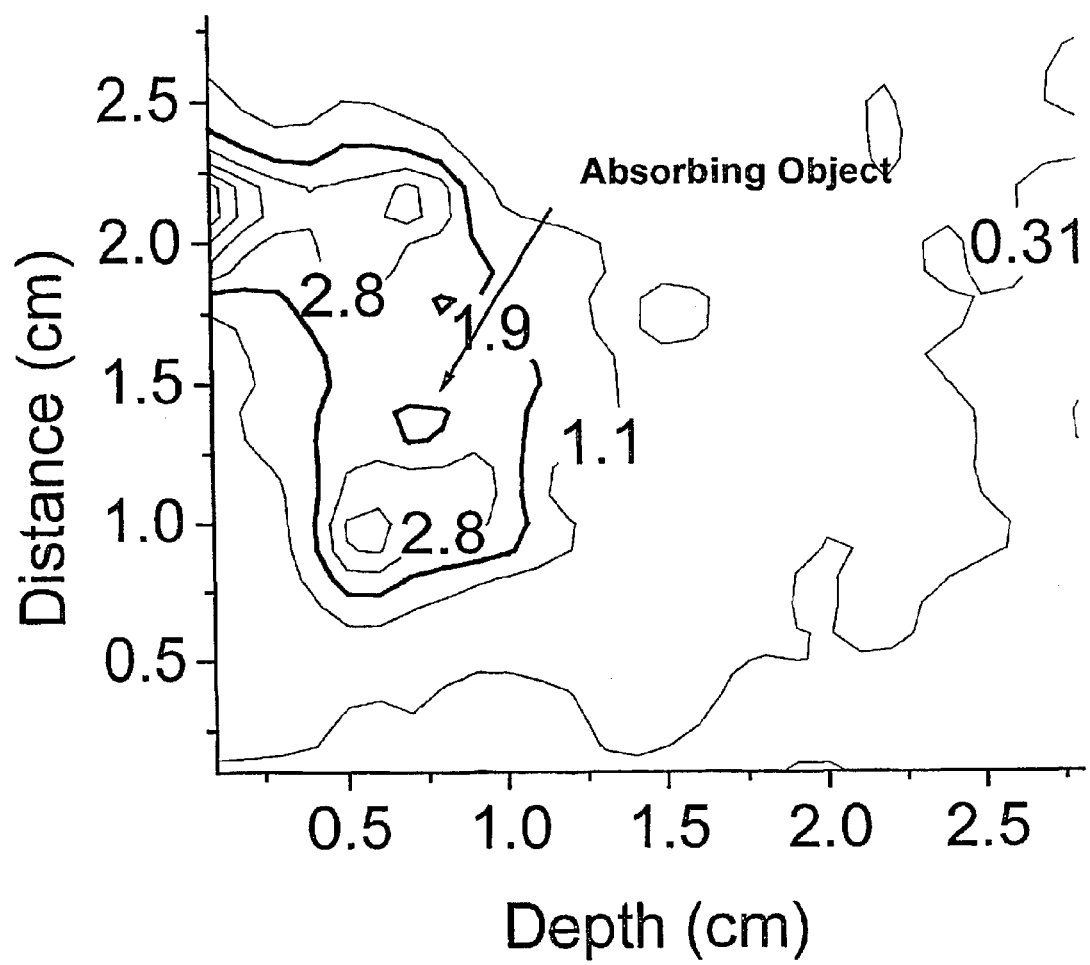
FIG. 11 illustrates the experimental results in the form of the power spectrum at the ultrasound frequency after background removal as a function of the position of the transducer, for another example of the invention, where a small absorbing region made of the Agar gel with the addition of black Agar is introduced.

FIG. 11 illustrates the experimental results in the form of the map of absorption (values of the power spectrum at the ultrasound frequency after background removal as a function of the position of the transducer) corresponding to the second example, where the presence of the absorbing agent AB is clearly observed.

Figure 12:
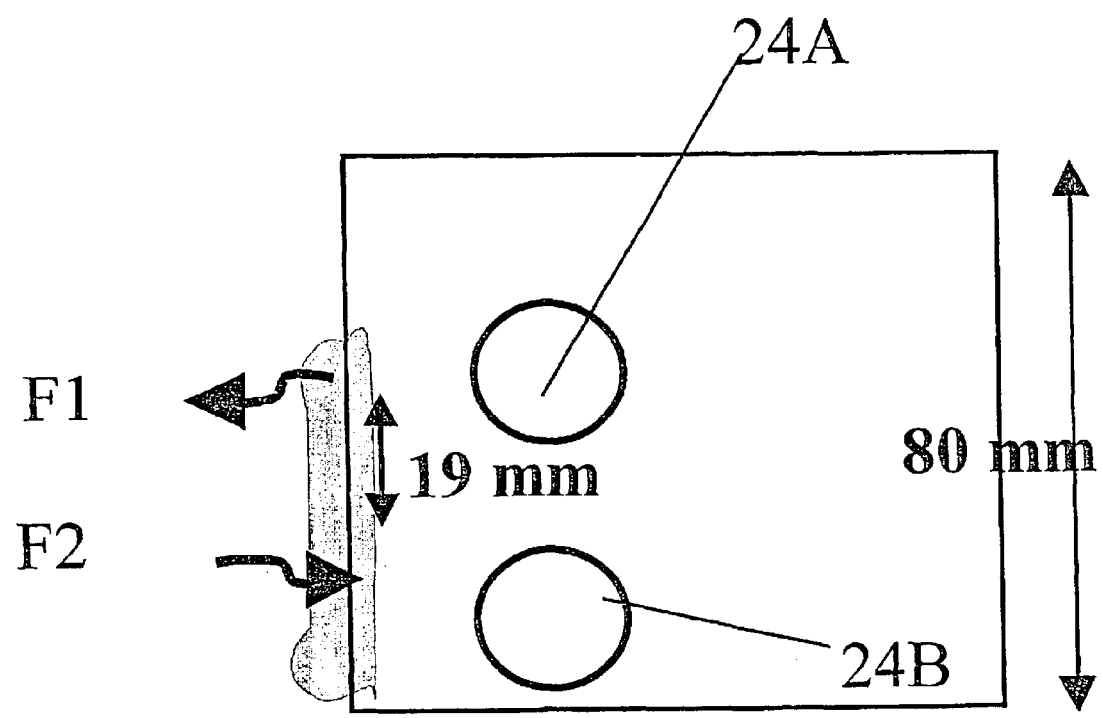
FIGS. 12 and 13 illustrate yet another experiment, where two transducers operated in parallel with different frequencies are used.
Figure 13:
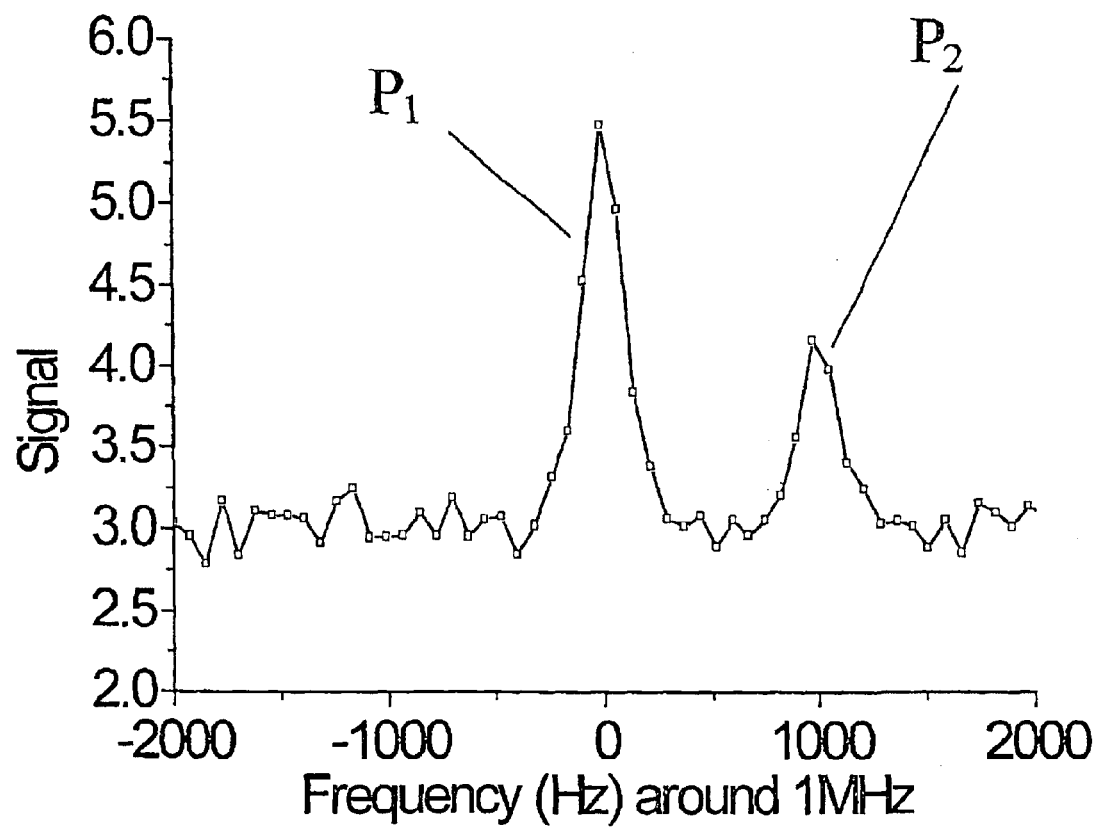

As indicated above, in order to get a two-dimensional image of the probed region (in the X-Y plane), it is possible to operate several transducers operating at different frequencies in parallel. In that case, the optical signal that is detected carries the information on photons that passed through each of the localized ultrasound waves. The following experiment was performed. As shown in FIG. 12, two transducers 24A and 24B were operated in parallel with frequencies 1 MHz and 1.001 MHz, respectively, at fixed positions. The transducers were coupled to a phantom made of regular Agar gel (index matching gel) that mimics tissues optical and ultrasonic properties. Light was coupled to the sample in a reflection configuration, similarly to the experiment with scanning ultrasound. Other experimental conditions were the same as described above. The power spectrum so obtained (after digital processing) is shown on FIG. 13. Two clear peaks $P_1$ and $P_2$ were detected at the transducers' frequencies. These two peaks represent the signals of the interaction between light and the localized ultrasound waves within the Agar sample.

Hence, by combining the use of several transducers arranged in the spaced-apart in the X-Y plane and operating at different frequencies, with the use of phase controlled ultrasound pulses, it is possible to obtain, in real-time, a three-dimensional picture of the absorbing regions in the tissues. The transducers' array may be of the direct array configuration or phase array configuration. In the case of a direct array, each transducer is independent and provides its own beam. Each transducer has its own, independent control channel. This configuration is particularly suited for a relatively small number of channels. In the case of phase array, all the transducers contribute to all the beams through a coherent effect. This configuration is particularly suited for a large number of channels. The phase-array concept is well-known in the medical ultrasound community. According to the present invention, the transducer phase array operates with several frequencies, rather than one frequency as conventionally used.

Figure 14A:
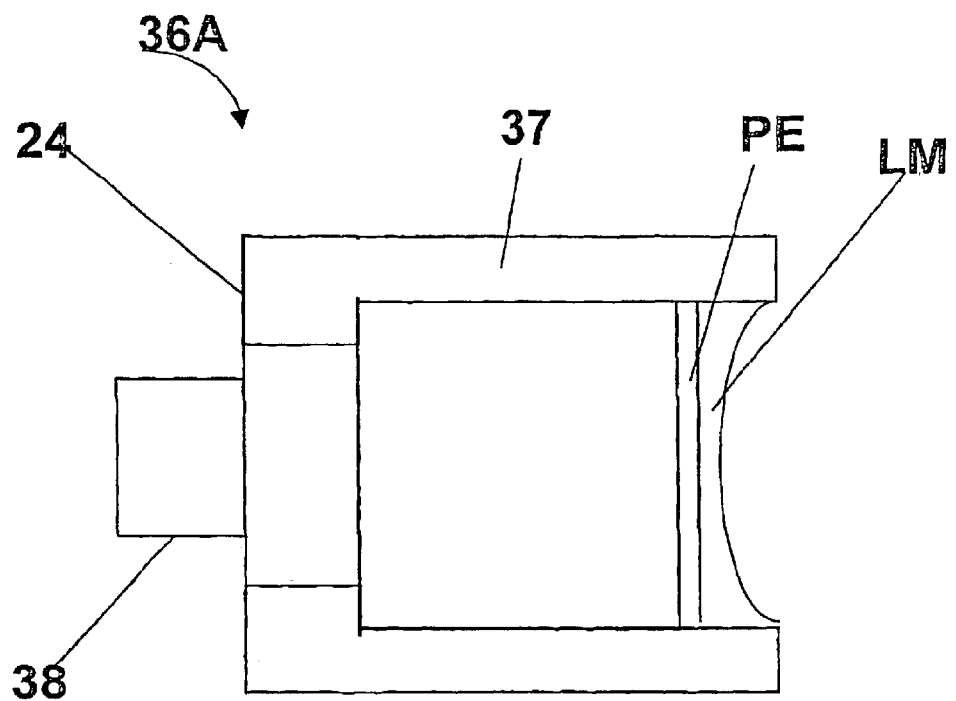
FIGS. 14A and 14B illustrate, respectively, a structure of a monolithic ultrasound probe (suitable to be used in a direct transducers' array) utilizing a single transducer, and the typical profile (pulse envelope) of an ultrasound wave generated by this transducer.
Figure 14B:
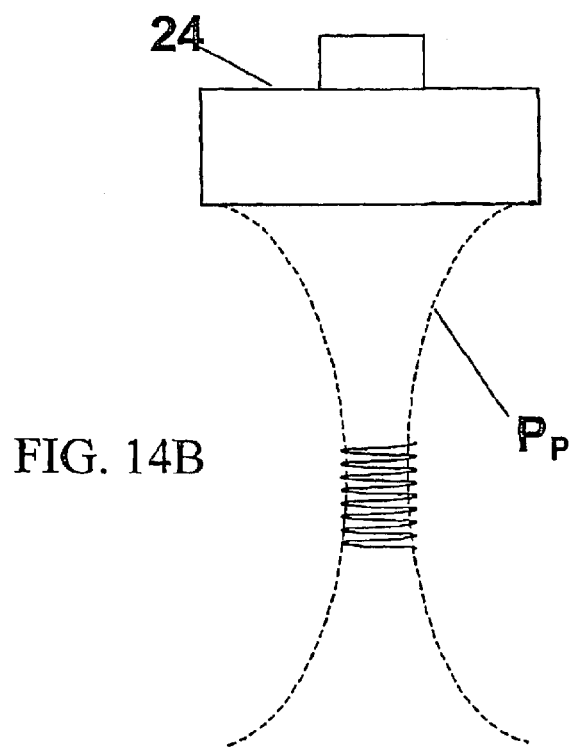

FIG. 14A shows a structure 36A of a monolithic ultrasound probe (direct transducers' array). In the example of FIG. 14A, a single-element focused transducer 24A accommodated in a transducer housing 37 is shown. The transducer is operated by electrical signals supplied through an electrical connector 38. The structure 36A makes use of a piezoelectric element PE as well as an ultrasonic lens and matching layer LM. The typical profile (pulse envelope) $P_P$ of an ultrasound wave generated by the transducer 24A is shown in FIG. 14B.

Figure 15A:
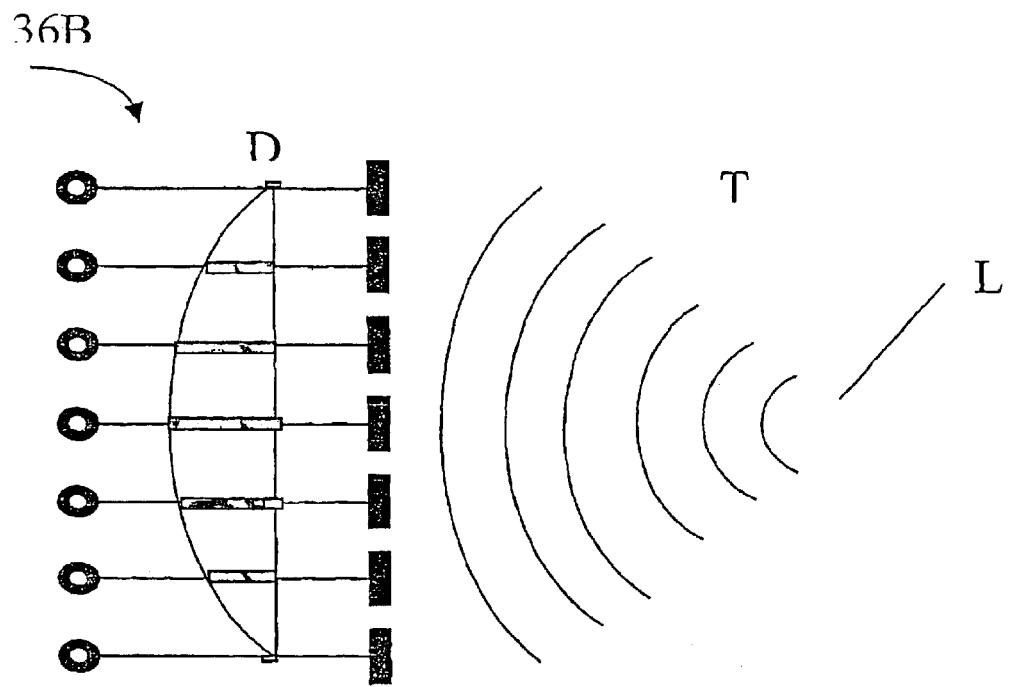
FIGS. 15A and 15B illustrate the principles of operation of a phase array based structure, wherein FIG. 15A corresponds to the focusing with an array transducer in transmission.
Figure 15B:
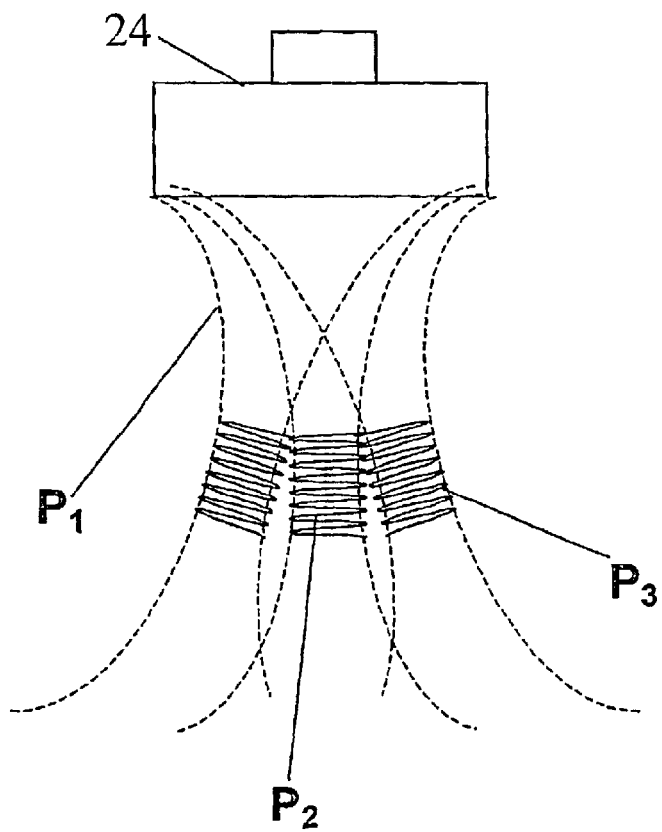

FIGS. 15A–15B illustrate the principles of operation of a phase array based structure 36B. FIG. 15A corresponds to the focusing with an array of transducers in transmission. The phase array structure uses an electronic delay scheme. As shown in FIG. 15A, delay lines DL are applied to the transducer elements, respectively, to provide delayed electrical excitations of the transducer elements to thereby generate a focused waveform of a transmitted wave TW at a certain location L in the medium. FIG. 15B illustrates the profile (pulse envelopes $P_1$, $P_2$ and $P_3$) of the phase array probe 24B operating with three different frequencies and creating several spatially resolved focuses along the Z-axis.

It should be noted that relative delays (or phases) between the different elements of the phase array determine the spatial shape of the envelope, and not the time variations of the ultrasound wave. In this sense, the time modulation (and therefore the Z-dependence) and the spatial shape of the ultrasound envelope are independent.

Both the monolithic ultrasound probe and the phase array structures are operable to perform the same function: focusing an ultrasound wave in a certain region in the space. The configurations are equivalent in that they are capable of simultaneously focusing different ultrasound pulses of different frequencies at different locations in the XY plane. The advantage of using the phase array is that the focus can be electronically adjusted, due to the fact that the different delays are not fixed but are electronically adjustable.

The following is the description of the spatial scanning of the X-Y plane by using the direct transducers' array configuration.

Each transducer delivers an ultrasound pulse of the form:

$$\Re\left(Ae^{i(2\pi f_p t + \varphi_p)}\right)$$

wherein $f_p$ is the transducer's frequency located at the position $X_p$, $Y_p$, 0), A is the ultrasound pulse's amplitude, and $\Phi_p$ is the phase of the ultrasound pulse. The pulse each channel delivers is a pencil-like beam, with a well-defined diameter (which gives the resolution in the X-Y plane).

The transducer array contains closed-packed transducers transmitting pencil-like beams of a diameter defined by the required resolution. Practically, however, it may be difficult to obtain, since small sized transducers typically have a large beam divergence.

Figure 16:
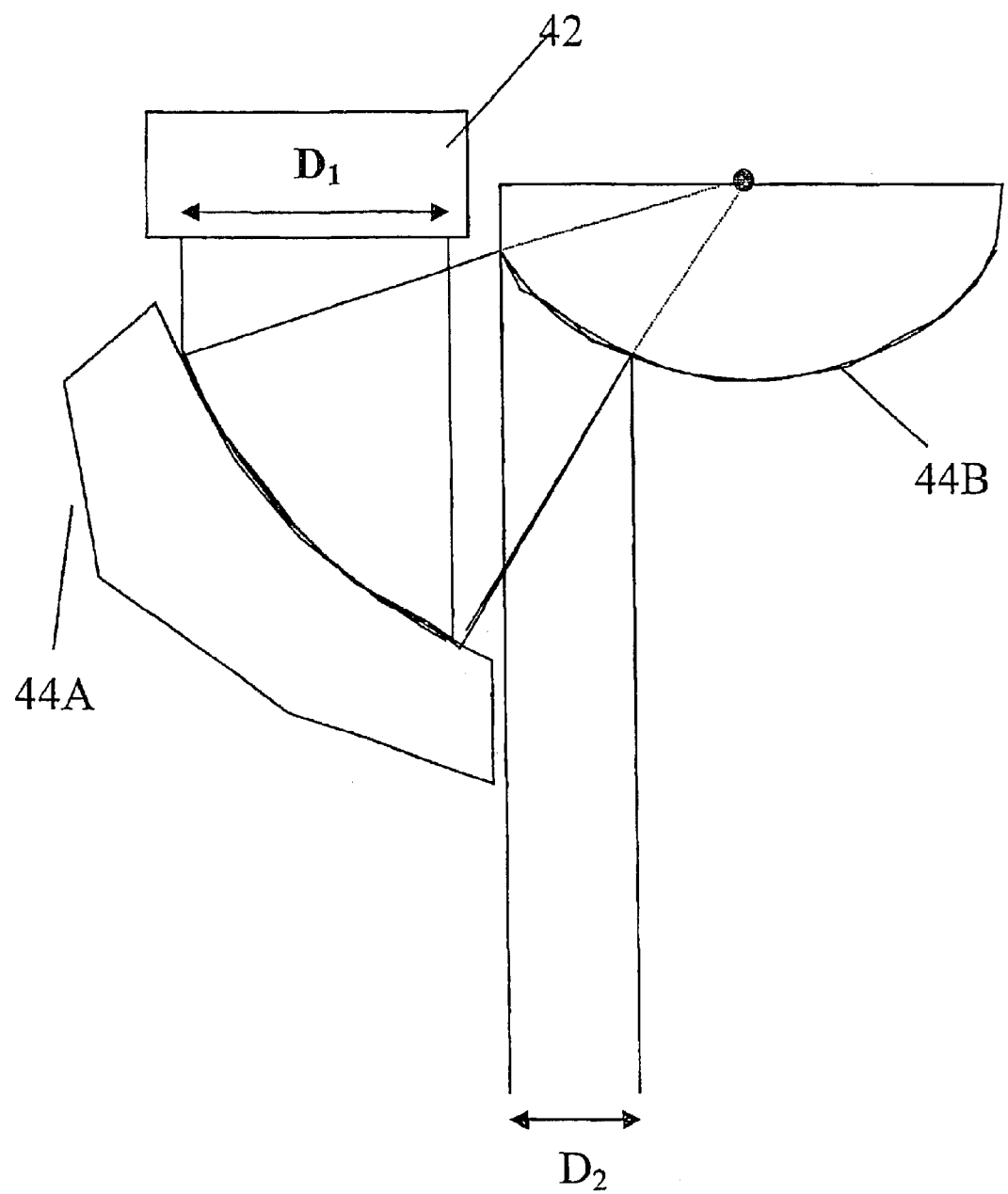
FIG. 16 illustrates an example of a transducer arrangement according to the invention aimed at exciting closely located points in the medium by regular size (large) transducers.

FIG. 16 illustrates an example of a transducer arrangement 40 according to the invention aimed at solving the above problem, namely, at exciting closely located points in the medium by regular size (large) transducers. The transducer arrangement comprises transducers' array 42 composed of large transducers closed-packed on a plane surface, and two reflective paraboloids 44A and 44B. The paraboloids are designed such that the focus ratio of the paraboloids equals the requested size reduction and the foci of the two paraboloids coincide.

Thus, a plurality of ultrasound beam generated by the transducers form together a tube of a diameter $D_1$. This tube-like beam impinges onto the concave surface of the paraboloid 44A and, while being reflected therefrom, propagate within a solid angle towards the convex surface of the paraboloid 44B, which reflects the beam and shapes it like a tube of a smaller diameter $D_2$. The two paraboloids actually act as a reflective telescope. The exact orientation of the paraboloid axes depends inter alia on the precise size of the transducers' array and the orientation of the exit ultrasound waves. In order to avoid aberration of each individual ultrasound beam emitted by each transducer, the paraboloids may be replaced by polyhedrons that maps the paraboloid surface so that each individual beam is reflected by a plane surface. In order to reduce the travelling distance of the ultrasound beams before they exit the transducer arrangement, the first paraboloid 44A can be removed, and the set of transducers are located on an imaginary paraboloid such that the beams all meet at the focus of the second paraboloid 44B.

The following is a specific numerical example. Sixteen transducers are used, each having a 1.25"-diameter, a 200 mm curvature. These 16 transducers (arranged at a 4×4 matrix), have an operating frequency of 1 MHz. This corresponds to a beam diameter of 6.5 mm at 6 dB. The beginning of the focal zone starts at about 77 mm from the transducer and finishes at about 191 mm from the transducer. A simple geometric analysis shows that the use of two paraboloids with focal distances of 10 cm and 2 cm, respectively, reduces the cross section of the ultrasound beam generated by the 4×4 matrix of transducers from 15 cm to a 5 cm-diameter beam exiting from the transducer arrangement.

The following is the description of the embodiment of the invention where the phase-array transducer configuration is used.

In the phase array configuration, the ultrasound beam delivered by each transducer strongly diverges, so that it can interfere with the beams emitted by the other transducers. When using the conventional phase-array one-frequency configuration of n transducers, each transducer emits a wave of the form:

$$\Re\left(Ae^{i(2\pi f t + \varphi_j)}\right)$$

wherein f is the transducer's frequency. The total complex amplitude at the point of coordinates (x,y,z) is:

$$A^2\left\{n + \sum_{\substack{j,k=1 \\ j\neq k}}^{n} \exp i\left(\frac{2\pi f(d_j - d_k)}{v} + \varphi_j - \varphi_k\right)\right\}$$

where $d_j = \sqrt{(x-X_j)^2 + (y-Y_j)^2 + z^2}$ is the distance between the point and the $j^{th}$ transducer with coordinates $X_j$, $Y_j$, 0), and v is the speed of sound in the tissues.

In order to maximize the intensity at the point z, it is necessary that all the phase terms equal to zero, i.e.:

$$\frac{2\pi f(d_j - d_k)}{v} + \varphi_j - \varphi_k = 0 \text{ for every } j, k.$$

This gives (n−1) independent equations that fix the relative phases of all the transducers. When dealing with the case of multiple frequencies according to the invention, each transducer emits a wave of the form:

$$\Re\left(A\sum_{p=1}^{P} e^{i(2\pi f_p t + \varphi_{j,p})}\right)$$

wherein P is the total number of frequencies. Hence, the total instant intensity is as follows:

$$A^2\left(n + \sum_{p,q,j,k} e^{i(2\pi(f_p - f_q)t + \varphi_{j,p} - \varphi_{k,q})}\right)$$

The oscillating term is not zero in average, only if $f_p = f_q$. The average intensity at the point (x,y,z) is therefore as follows:

$$A^2\left(n + \sum_{p,j,k} e^{i(2\pi f_p(d_j-d_k)+\varphi_{j,p}-\varphi_{k,p})}\right)$$

The average intensity is maximized, when the term under the exponential is nul, that is:

$$2\pi f_p(d_j-d_k)+\Phi_{j,p}-\Phi_{k,p}=0$$

For a specific frequency $f_p$, and a given point $M_p$ with coordinates $(x_p, y_p, z_p)$, i.e., a given set of values $d_j$, a series of (n−1) equations is obtained that fixes the relative values of the phases $\Phi_{j,p}$. It is thus possible to define, for each frequency, a different point at which the ultrasound intensity will be maximal. The number of frequencies, and consequently the number of points probed in the sample, can be much larger than the number of transducers. The same is valid in the case of direct transducers' array. In the case of phase-array, however, the waveform in the LUT is more complex, and all the DDS are related one to the other. More specifically, the waveform that must be introduced in the LUT of the $j^{th}$ transducer is not a simple sinusoidal curve, but is as follows:

$$\Re\left(A\sum_p e^{i(2\pi f_p t+\varphi_{j,p})}\right)$$

wherein the frequencies $f_p$ are chosen so that there is minimum cross-talk between the signals after the power spectrum procedure, and the bandwidth of the transducers is optimally filled. The phases are chosen so as to obtain a uniform array of points in the X-Y plane and to provide scanning of the Z-direction by this plane. This is obtained by solving the following equations:

$$2\pi f_p(d_j-d_k)+\Phi_{j,p}-\Phi_{k,p}=0$$

for each position. This calculation is made once, and the resulting waveforms are then stored in the LUT of each DDS. The rest of the scheme (external clock and phase matching) is identical to the case of the direct transducers' array.

With regard to array of amplifiers in the phase array case, similarly to the above-described case of the direct transducers' array, the signal from the DDS is sent to the amplifier that matches the transducers needs. The amplifier must have a fast enough rise time (typically ten times shorter than the inverse of the transducer's highest frequency). After the amplifier stage, the signal is sent to the transducer.

In the case of the phase array, the transducers' array is a two-dimensional flat array of identical, small size transducers. The larger the number of transducers, the better the resolution. For example, for an array made of 16×16 transducers, assuming that each frequency needs a bandwidth of 1 kHz in order to avoid cross-talk, a necessary bandwidth for the transducers is about 300 kHz, requiring a cavity factor Q of about 3, which is reasonable. The size of each transducer is smaller than the ultrasound wavelength. The design and fabrication technology of such arrays is known per se and therefore need not be specifically described.

With regard to the illuminator, the following should be noted. In order to obtain the oxygen saturation, it is known to use two or more different wavelengths of incident light. To this end, lasers with several constraints, such as a long coherence length and sufficient power, are used.

Different techniques can be used to couple the light in and out the medium (patient's body) such as direct coupling from the laser (using mirrors and lenses), the use of fibers, etc., provided trespassing of the limit imposed by biological damages is avoided.

Figure 17:
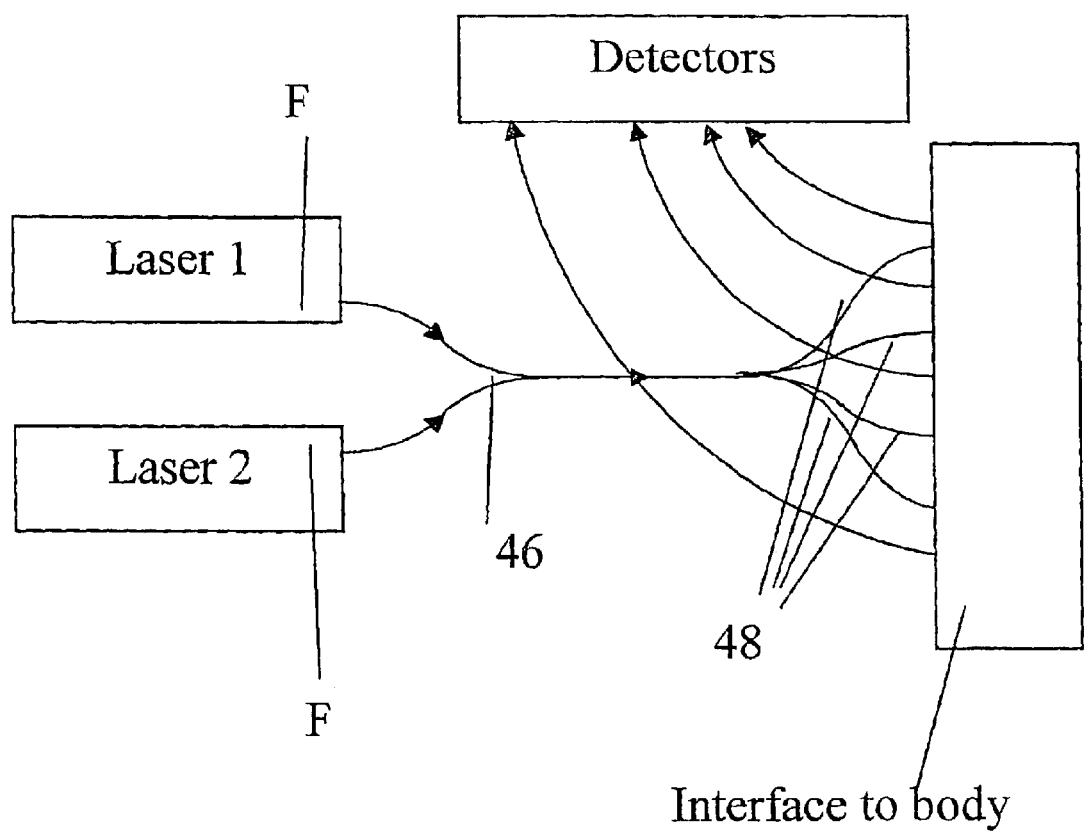
FIG. 17 illustrates the light direction towards the region of interest in the medium utilizing optical fibers.

If coupling of light from the laser to an optical fiber is used, as shown in FIG. 17, such a fiber F can itself be coupled to a coupler 46 with several branches, generally at 48. This provides better filling of the tissues with light and reducing the local amount of light delivered to the tissues while keeping an overall larger amount of light. A holographic diffuser can be attached at the output of each branch in order to control the shape of the input light distribution when it enters the tissues.

One of the most important points in any imaging technique is to obtain a good enough signal to noise ratio (SNR). The improvement of the signal to noise ratio in the detected signals according to the invention consists of matching the statistical trace length with the speckle decorrelation time $\tau_0$, i.e, the phase-shift is only on average occurring at the time $\tau_0$. By introducing a statistical model of the speckle fluctuations, and by fitting the experimental results with the model, the signal to noise ratio can be significantly improved.

According to the statistical model, in order to estimate the signal to noise ratio at the detector, the signal arriving at the detector should be analyzed. The image at the detector is a speckle pattern. This pattern fluctuates in time, and its probability distribution is well-known. The signal also fluctuates between power spectra. The statistical model based approach simply averages these spectra. A better alternative is to use the statistical models and fit the data to the model.

The advantage of this statistical approach is that it is possible to converge much faster to the signal value. The procedure consists of the following: A series of n power spectra is obtained. One ultrasound frequency is selected, and the values of the n spectra at this frequency (signal) are stored. What is then selected are p points around this frequency, where no ultrasound beam is present. By this, a noise reference is defined. The n×p values of the noise (background) are stored. The normalized histograms of the noise (background) and of the signal are determined, and fitted to the Rayleigh distribution. Then, the noise fitted average is subtracted from the signal fitted average.

Figure 18:
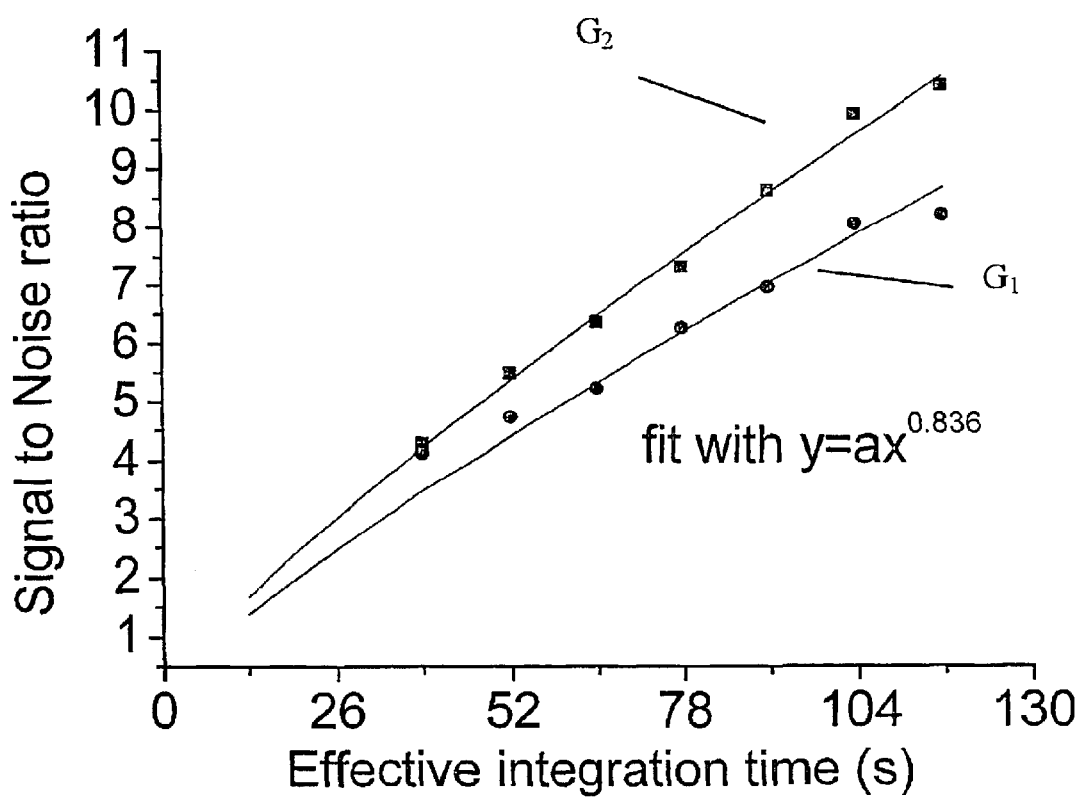
FIG. 18 illustrates the experimental results showing the signal to noise ratio as a function of the integration time for both rough data and fitted data with a Rayleigh function.

Experimental results (taken with an ultrasound probe focused at a distance of 30 mm) are illustrated in FIG. 18, showing two graphs $G_1$ and $G_2$ corresponding to the signal to noise ratio as a function of the integration time for, respectively, the rough data and the fitted data with a Rayleigh function. The fitted data have a higher S/N than the non-fitted data, up to a 30% factor (in these data, the background has been removed).

The measurement that is performed by the apparatus of the present invention is a measurement related to the local light intensity, and not directly to local absorption. In order to retrieve the absorption, it is necessary to perform a reconstruction procedure. A simple reconstruction procedure is to simply use the known Beer-Lambert law. However other reconstruction procedures are possible as well (for example, Monte-Carlo simulation, numerical resolution of Maxwell equations, etc.).

Once the local absorption is retrieved at several wavelengths, the tissue saturation index can be easily retrieved from the ratio of the absorption coefficients at different wavelengths. This procedure is well-known in the art and has been extensively used in the field of near-infrared spectroscopy.

The apparatus according to the present invention can be used for diagnostic purposes, namely, for diagnosing an abnormality, or monitoring a patient in order to detect the appearance of such an abnormality; control of a therapeutic treatment; diagnostic and monitoring. The device can be used as a monitoring device, for example in the case of brain trauma, where a secondary injury can appear several hours after the primary injury. In that case, the device maps the region surrounding the trauma and looks for changes in the absorption that witness changes in the oxygenation of the tissues. The device can be used for the diagnosis of cancerous tumors. The latter are known to generate a large number of capillaries that sustain their existence. Therefore, the amount of blood that is present in the area surrounding a tumor is much larger than in non-cancerous tissues. Tumors can therefore be detected and monitored.

The apparatus according to the invention can be used for controlling therapeutic treatment. If a therapeutic treatment generates modifications in the absorption or scattering of tissues locally, either using endogenous or exogenous agents, these changes can be monitored using the present invention. For example, local laser ablation or cryogenic treatment of tumors would result in a change in the optical properties that can be detected and monitored using the device. Other therapeutic means such as chemical or radiation therapy can be monitored in a similar way.

The technique of the present invention can be used to monitor temperature within the body. It has been demonstrated that the Brownian motion of particles can be very accurately determined using diffusive light (D. J. Pine et al. "Dynamical correlations of multiply-scattered light", Scattering and Localization of Classical Waves in Random Media, Ping Sheng ed. World Scientific (1990)). Early works on diffusive light spectroscopy have shown that it was possible to differentiate between the Brownian motion of the particles and the motion occurring due to the ultrasound (W. Leutz and G. Maret, "Ultrasonic modulation of multiply scattered light", Physica B, 204, 14–19, (1995)).

When there is no or very little particle fluctuations, the optical signal obtained at the ultrasound frequency, using the algorithm described above, has a peak whose fill width at half maximum (FWHM) is as narrow as the ultrasound peak FWHM. However, when particles are fluctuating, their velocity due to the local fluctuations will be added to their velocity due to the ultrasound, and the peak FWHM at the ultrasound frequency will increase due to the Doppler effect. Since the local temperature is proportional to the square root of the local particles velocity, this gives a way to locally evaluate the temperature.

A second effect that also contributes to evaluating the local temperature is the fact that when particles fluctuate, there is a loss of coherence in the signal translated into an increase in the FWHM of the detected signal.

Both effects go in the same direction (increase in the FWHM with increasing temperature). The precise relation between changes in the fluctuations and $\Delta T$ can be obtained empirically (for example, by comparing these measurements with measurements obtained by invasive methods). A lookup table (LUT) can then be used for relating the changes in the FWHM and local temperature. By scanning the ultrasound focus, a temperature map can be obtained.

In the above-described examples, the location of the interactions between the light and ultrasound radiation at different points along the Z-axis was achieved by controlling the phase between successive ultrasound pulses. Alternatively, different Z-points can be located by sequentially affecting the phase of the light signal without the need of controlling the phase of the ultrasound pulses, and without the need of a fast detector.

Turning back to FIG. 1B, the function generator may be operable to modulate the output intensity of the laser using a phase modulation scheme. In this case, the generation and transmission of ultrasound pulses may be implemented in the conventional manner. In order to scan the X-Y plane by the plurality of transducers, the transducers may be operated either sequentially or with different frequencies of ultrasound pulses. Additionally, in this case, there is no need for using fast detector(s), but rather a "slow" detector, such as a CMOS camera, which can be used and allows parallel detection of a plurality of light components (by means of a matrix of pixels). The laser light is modulated with a fixed frequency and a modulated phase. The fixed frequency can be chosen arbitrarily, for example near the ultrasound frequency so that the difference between both frequencies is smaller than 100 kHz. The modulated phase is built so that when successive ultrasonic pulses pass through the same position, the laser phase is slightly shifted, the shift being different for each different position of the ultrasound pulse.

When diffuse light passes through the ultrasound pulse, it gets partly modulated and the modulated signal time dependence is a sinusoidal signal, whose argument is the difference between the ultrasound and laser modulations' arguments. It is therefore composed of a fix frequency and a modulated phase. An optical detector then detects this optical signal.

According to one example, the detector response time is smaller than or equal to the ultrasonic pulse-to-pulse periodicity. Therefore, for a given ultrasonic pulse firing, the detector receives an optical signal that is the time integration of several signals corresponding to the different spatial positions of the ultrasound pulse.

For a given ultrasonic pulse position, after a time delay corresponding to the ultrasonic pulse-to-pulse periodicity, a new ultrasound pulse, identical to the previous one, occupies the same spatial position, and so on. Since the laser modulation is built so that there is a slight phase-shift between two successive ultrasonic pulses, the light-ultrasound interaction signal has a phase that is slightly shifted by a constant amount at each pulse firing. After several firings, for each pulse position a sinusoidal modulation is described. By choosing the laser phase-shift so as to be different for each spatial position of the ultrasonic pulse, the period of the sinusoid will be different for each ultrasound pulse position. The light-ultrasound interaction signal therefore is composed of a series of sinusoidal signals whose frequencies are related with a one to one correspondence with the pulse position, and whose amplitude is proportional to the photon density at the ultrasound position.

Figure 19:
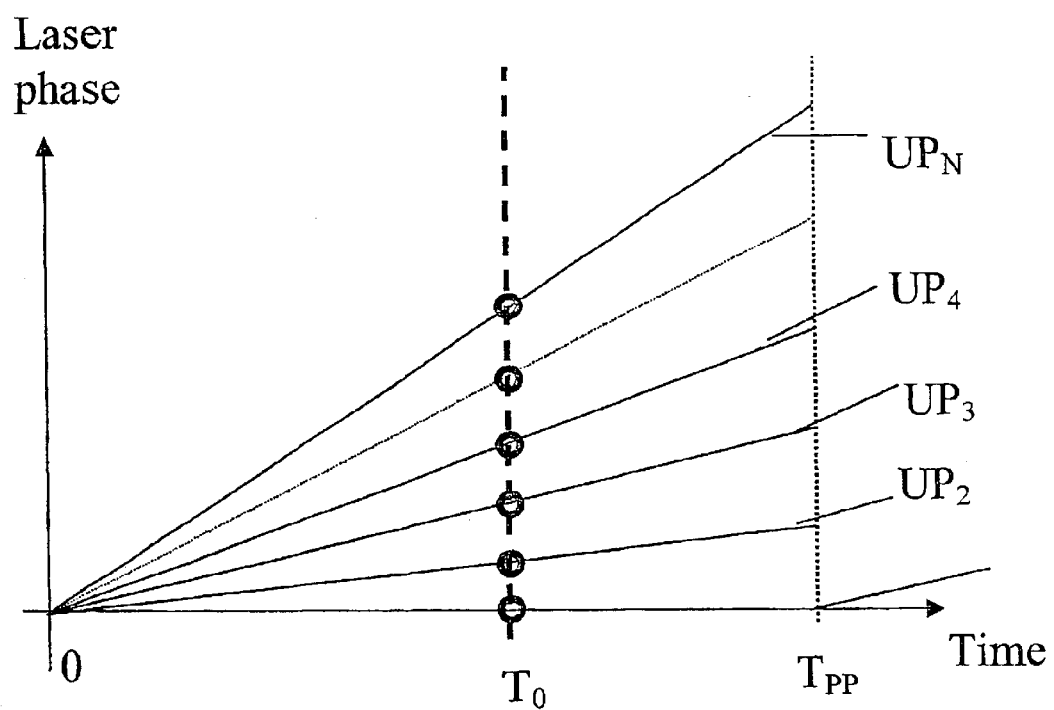
FIG. 19 illustrates the laser phase modulation scheme.

Referring to FIG. 19, there is illustrated the laser phase modulation scheme. Successive ultrasound pulses are represented with the same time origin (triggering time). The spatial position of a given ultrasonic pulse is associated with a given time of pulse propagation, namely, the propagation time divided by the speed of sound in the medium. For a given position of the ultrasonic pulse, successive pulses experience a different laser phase that is shifted by a given amount different for each position.

Figure 20:
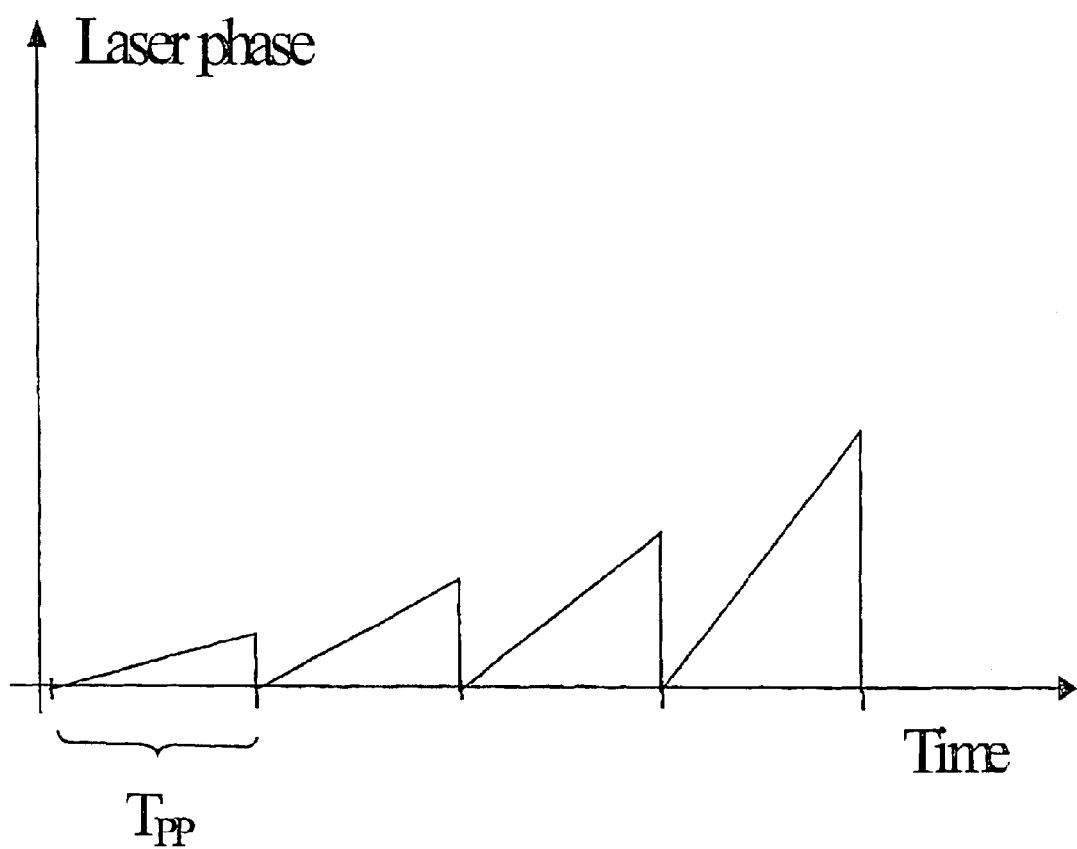
FIG. 20 illustrates the time dependence of the laser phase.

FIG. 20 illustrates the time dependence of the laser phase without folding. It is represented by a saw-tooth function with increasing tooth-size, the duration of each such tooth being defined by the ultrasound pulse-to-pule periodicity $T_{pp}$.

The phase-shift can be chosen so that the end value of the phase is always a multiple of $2\pi$. In this case, the phase will be continuous, which presents advantages for the electronic implementation. The laser phase can be chosen so as to be a continuous time function. For example, the laser phase can be chosen to be proportional to $t_1 t$, where $t_1$ is the relative time from the ultrasound pulse firing trigger, and t is the absolute time, from the start of the measurement session. In this case, the laser phase will have a quadratic dependence with the relative time.

Figure 21:
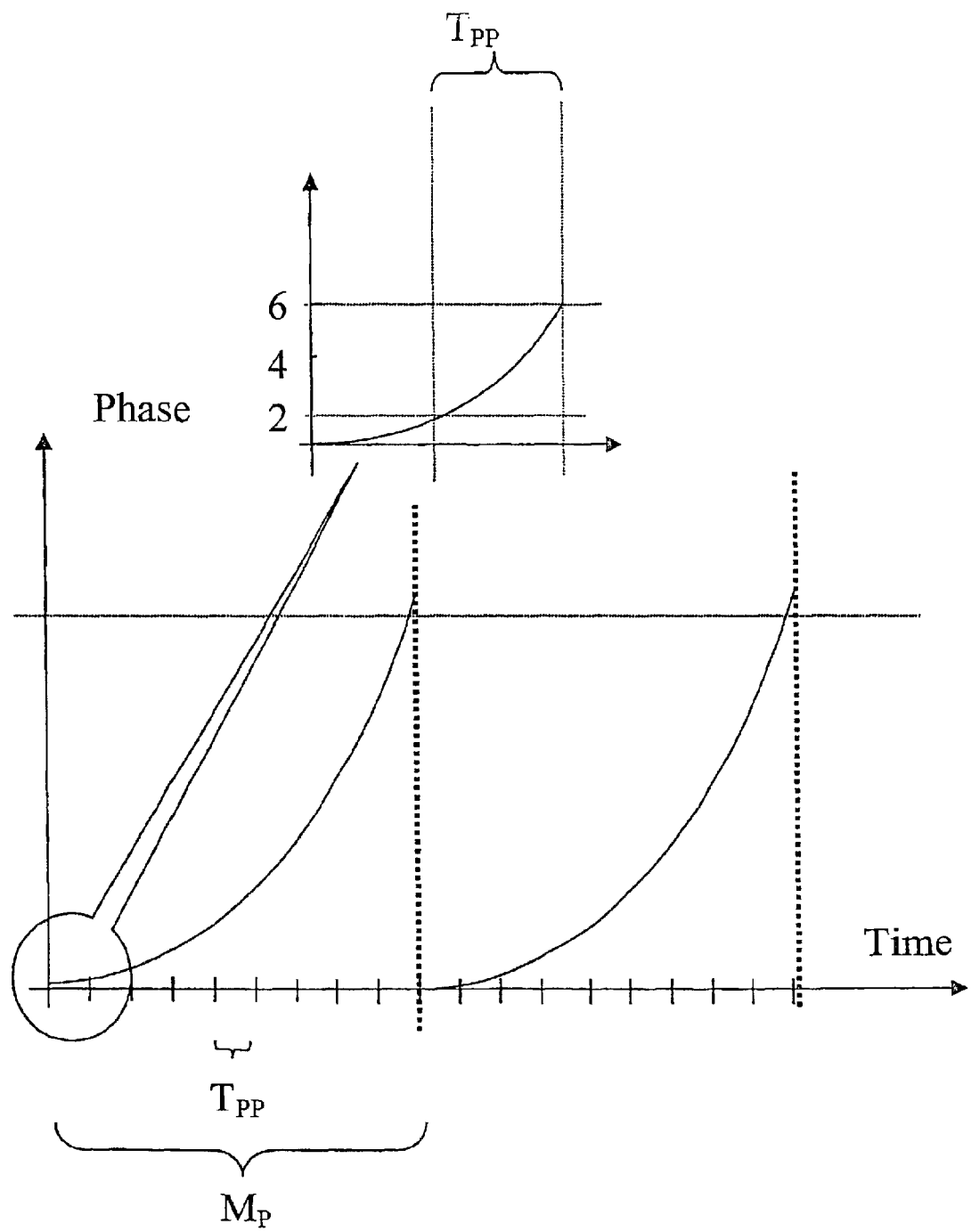
FIG. 21 illustrates the use of the continuous phase of the light signal.

FIG. 21 illustrates the use of the continuous phase, when both the $2\pi$-shift multiple is described during a pulse-to-pulse period and the phase is continuous with the time. The total measurement period MP is defined as the time necessary to obtain a complete sinusoidal period for the slowest no-null frequency. The total measurement time will be of the order of magnitude of one to several measurement periods.

In another example, the detector response time is larger than the pulse-to-pulse time duration $T_{pp}$. In this case, the laser modulation phase may be shifted only every several pulse-to-pulse periods, so that the same signal reaches the detector during the period of several ultrasonic pulses. This is an averaging operation.

Figure 22:
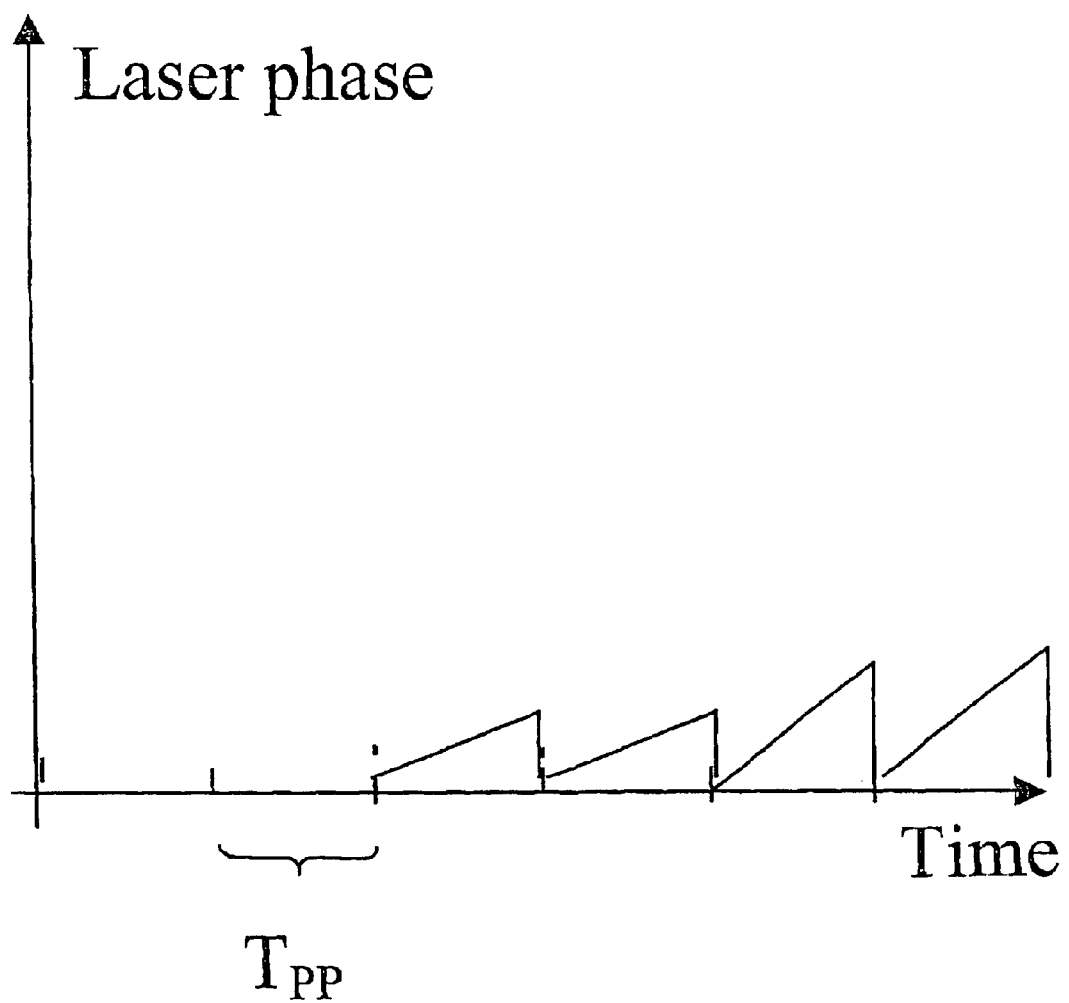
FIG. 22 illustrates an example of the phase sequence of the laser modulation scheme.

FIG. 22 illustrates the phase sequence of the laser modulation for the case of integrating a detector and average signal.

It should be understood that although the use of a single laser is exemplified, several lasers could be used in parallel. In this case, the fixed frequency of each laser can be chosen so that, after power spectrum, each laser occupies a different spectral band. The laser phase may be synthesized in real-time, or may be computed in advance and stored in a look-up table for faster access. The laser can be modulated either directly in the case of semiconductor lasers, through current modulation, or by using an external light modulator (such as an acousto-optics modulator)

It should also be noted that the light phase modulation concept can be utilized with the transducer arrangement composed of a single ultrasonic transducer, several transducers, phase-arrayed or not, operating with different frequencies. If several transducers are used, the fixed frequency of each transducer can be chosen so that, after power spectrum, each transducer occupies a different spectral band, each band corresponding to a different position in the plane perpendicular to the ultrasound wave propagation axis (X-Y plane).

Additionally, the modulation scheme of the laser light can be replaced by that of the detector. This includes the modulation of photomultiplier dynodes, if photomultipliers are used, or a multichannel plate modulation if multichannel plates are used in conjunction with a camera.

The following is the simulation example:
The laser modulation is chosen to be proportional to:

$$\sin(\Omega_{US} t + \alpha t_1 t + \beta t)$$

wherein $\Omega_{US}$ is the ultrasound central frequency, $t_1$ is the relative time starting from each ultrasonic pulse trigger, t is the time from the start of the total measurement; $\alpha$ is a positive constant; and $\beta$ is the difference frequency between the laser frequency and the ultrasound frequency.

The signal after the ultrasound-light interaction is proportional to $$\sin(\phi_L(t_1,t)) t$$

with $\phi_L(t_1,t) = \alpha t_1 t + \beta t$.

In the present example, the values $\alpha$ and $\beta$ are chosen of the effective frequencies to be: $\alpha = 3$ kHz/s and $\beta = 30$ kHz, and 6 points along the Z-axis (n=6) are supposed to be obtained. The pulse repetition rate is PRF=30 kHz. The averaging is carried out only once for the sake of simplicity. Therefore, the frequency $\omega_0$ is $\omega_0 = $PRF$=30$ kHz. The difference between two consecutive frequencies (signal frequencies) is 3 kHz. The total phase values are:

| Position in the Z axis\Time × 30 μs) | 0 | 1 | 2 | 3 | 4 | 5 | 6 | 7 | 8 | 9 | 10 | 11 |
|---|---|---|---|---|---|---|---|---|---|---|---|---|
| 0 | 0 | 1 | 2 | 3 | 4 | 5 | 6 | 7 | 8 | 9 | 10 | 11 |
| 1 | 0 | 1.1 | 2.2 | 3.3 | 4.4 | 5.5 | 6.6 | 7.7 | 8.8 | 9.9 | 11 | 12.1 |
| 2 | 0 | 1.2 | 2.4 | 3.6 | 4.8 | 6 | 7.2 | 8.4 | 9.6 | 10.8 | 12 | 13.2 |
| 3 | 0 | 1.3 | 2.6 | 3.9 | 5.2 | 6.5 | 7.8 | 9.1 | 10.4 | 11.7 | 13 | 14.3 |
| 4 | 0 | 1.4 | 2.8 | 4.2 | 5.6 | 7 | 8.4 | 9.8 | 11.2 | 12.8 | 14 | 15.4 |
| 5 | 0 | 1.5 | 3 | 2.5 | 6 | 7.5 | 9 | 10.5 | 12 | 13.5 | 15 | 16.5 |

Each column corresponds to a new ultrasonic pulse (30 microseconds time difference between two columns). In the linear form, the same is as follows:
0,0,0,0,0,0,1,1.1,1.2,1.3,1.4,1.5,2,2.2,2.4,2.6,2.8,3,3,3.3 . . . for one average, where the time difference between two points is 5 microseconds.

In the case of two averages, we have:
0,0,0,0,0,0,0,0,0,0,0,1,1.1,1.2,1.3,1.4,1.5,1,1.1,1.2,1.3,1.4,1.5, 2,2.2,2.4,2.6, . . . .

In the process of simulation, the sinus of the phase is performed and multiplied by a coefficient that simulates the local absorption (coefficients 1 to 6 for the positions 0 to 5 respectively).

Figure 23:
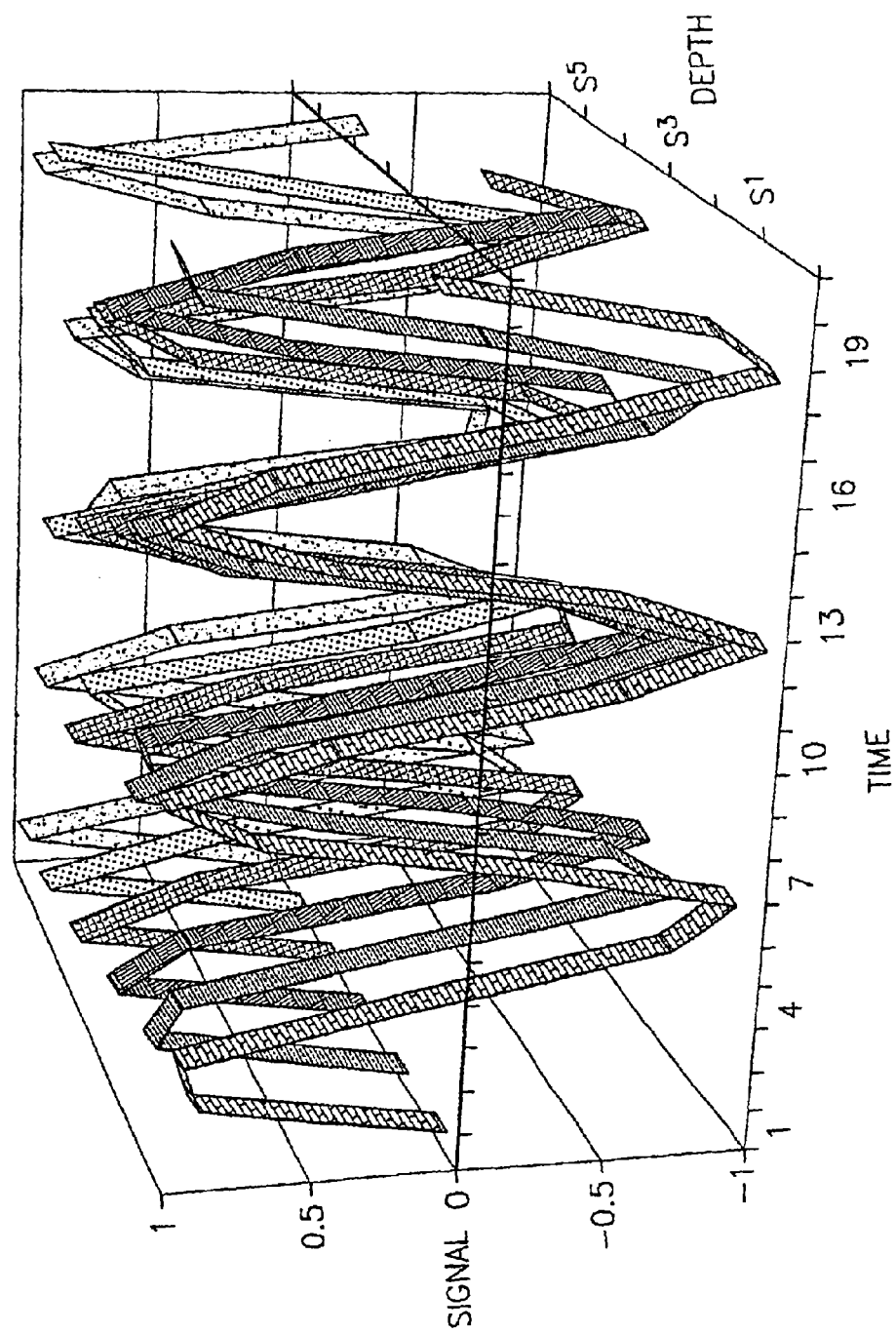
FIG. 23 illustrates the simulation results of generating different signals corresponding to the different positions of the ultrasound pulse.

Reference is made to FIG. 23, illustrating the different signals corresponding to the different positions of the ultrasound pulse. The summation of the contributions of all the frequencies gives the integrated signal received by the detector at each sampling time.

Figure 24:
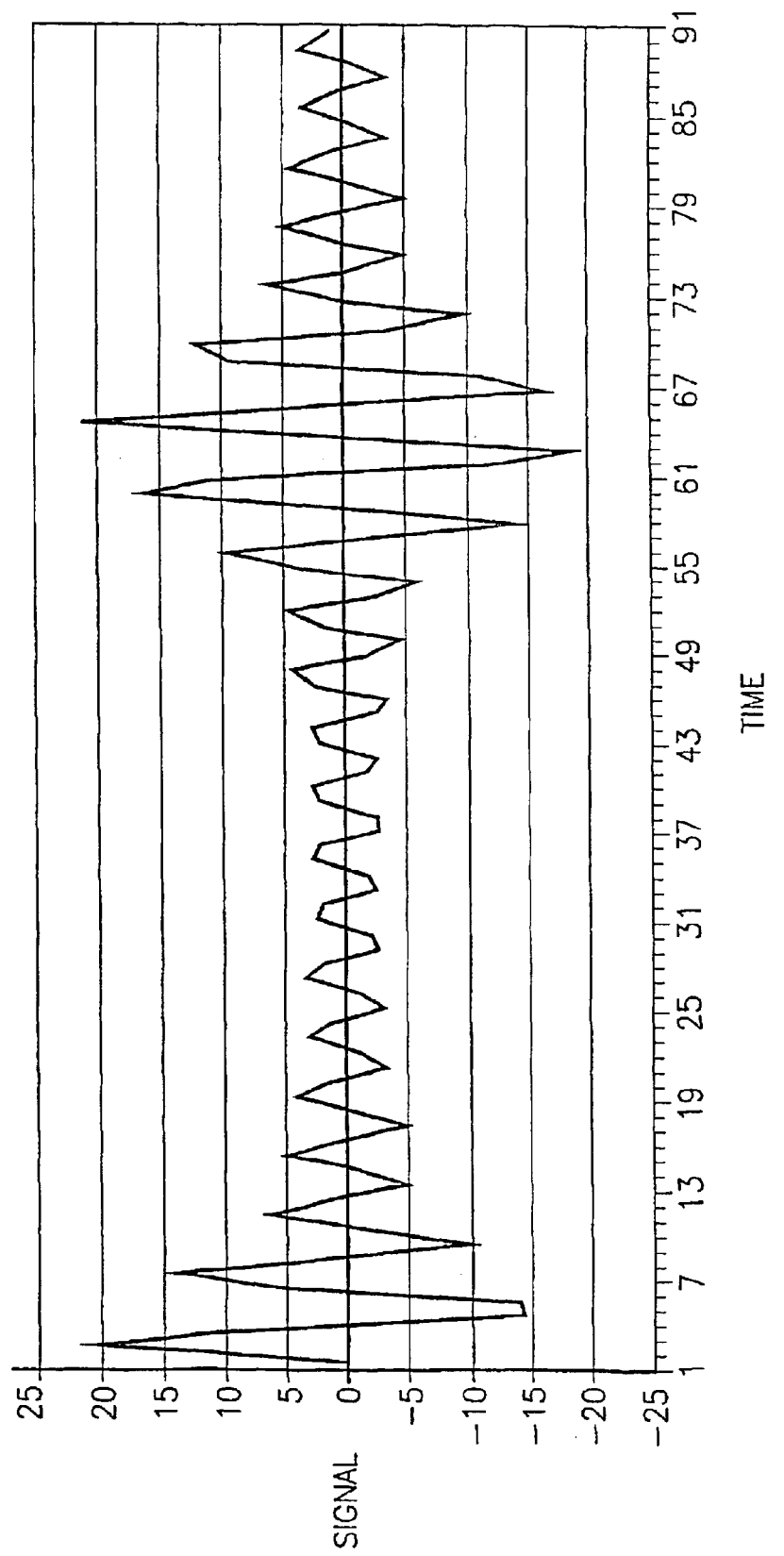
FIG. 24 illustrates the time variations of the detected light signal.
Figure 25:
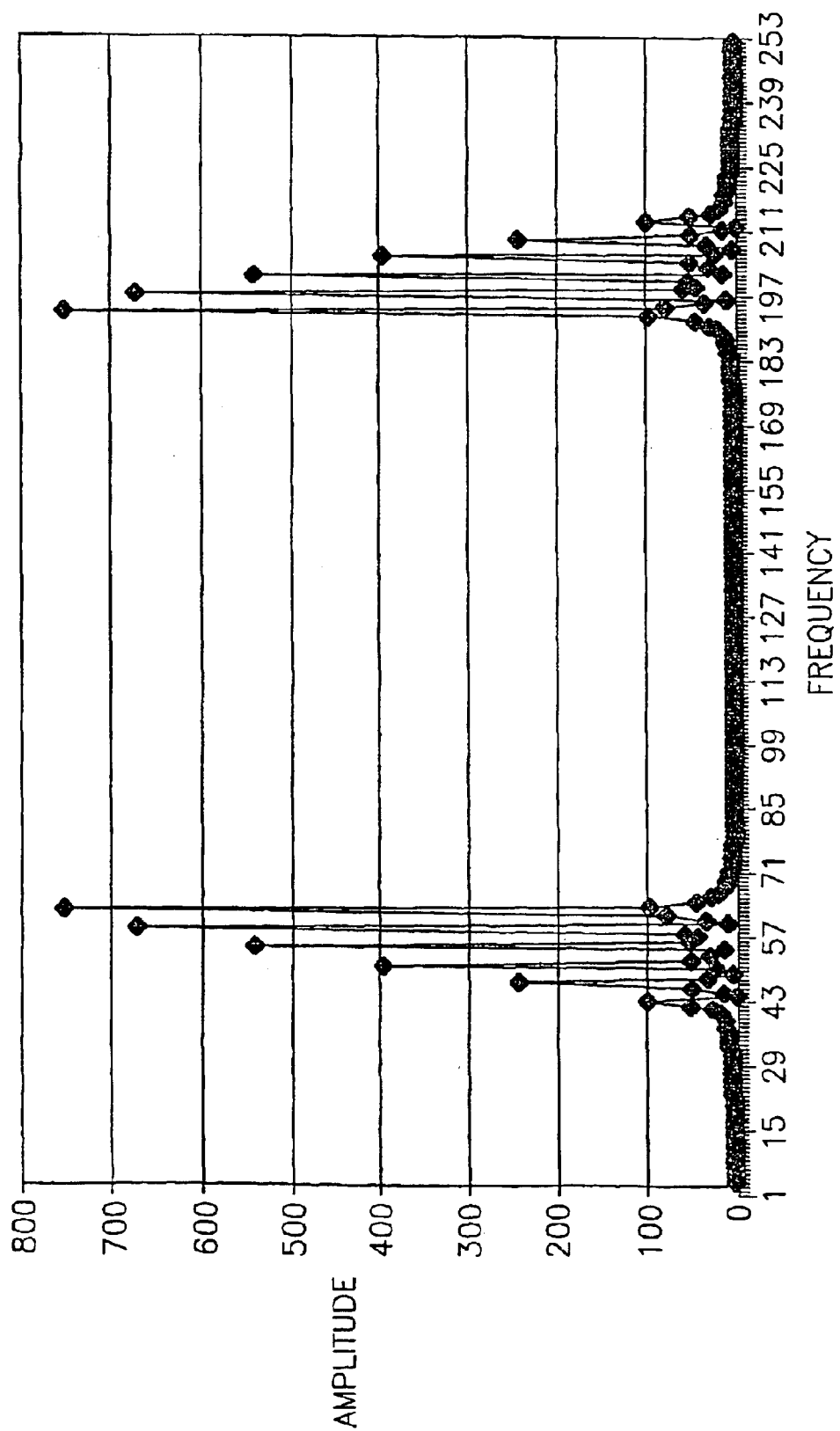
FIG. 25 illustrates the resulting spectrum showing the peaks corresponding to the modulated signals at different locations along the ultrasound propagation axis.

The time difference between the consecutive data is 30 microseconds. In case of two averages, the time would be 60 microseconds. FIG. 24 illustrates the time variations of the signal. This summation has been calculated for 256 sampling points. This is the slow signal detected by the detector. It should be understood that, in order to obtain the right time-scale, the time axis data must be multiplied by 30 microseconds. A power spectrum is then applied to the data and the resulting spectrum is illustrated in FIG. 25, showing 6 clear peaks, whose magnitude is proportional to the coefficients introduced (1,2,3,4,5,6).

Those skilled in the art will readily appreciate that various modifications and changes can be applied to the embodiments of the invention as herein before exemplified without departing from its scope defined in and by the appended claims.

What is claimed is:
1. A method of detecting an effect of interactions of electromagnetic radiation with ultrasound radiation pulses at different locations within a region of interest in a scattering medium to thereby enable imaging of said medium, the method comprising:

(i) generating a plurality of sequences of ultrasound pulses;

(ii) generating incident electromagnetic radiation of at least one wavelength;

(iii) transmitting the plurality of sequences of said pulses towards a plurality of locations, respectively, in said region of interest within an X-Y plane perpendicular to axes of propagation of the ultrasound pulses, while illuminating said region of interest with the incident electromagnetic radiation, to thereby produce signals of the electromagnetic radiation, each being a frequency modulated by a frequency of the ultrasound radiation and allowing identifications of said interactions that occur at said plurality of locations in the X-Y plane and in a plurality of location along the Z-axis;

(iv) detecting the modulated signals of the electromagnetic radiation and generating data indicative thereof, the analysis of said data enabling the imaging of the region of interest the method being characterized in that:

each of said generated ultrasound pulses comprises at least one sinusoidal cycle and said generated electromagnetic radiation is in the form of a modulated continuous wave, the method thereby enabling control of a phase of either the ultrasound or the electromagnetic radiation to provide a phase continuity of the detected modulated signals.

2. The method according to claim 1, wherein, in step (iii), said plurality of sequences are transmitted to the different locations in the X-Y plane by scanning the X-Y plane with a single transducer.

3. The method according to claim 1, wherein, in step (iii), said plurality of sequences are transmitted to the different locations in the X-Y plane by scanning the X-Y plane with a one-dimensional array of transducers aligned along the X-axis.

4. The method according to claim 1, wherein, in step (iii), said plurality of sequences are transmitted to the different locations in the X-Y plane by means of a two-dimensional array of transducers aligned along the X- and Y-axes.

5. The method according to claim 1, wherein said sequences of pulses have different frequencies.

6. The method according to claim 3, wherein said array of transducers is a multi-frequency phase array, the method comprising electronically controlling the phases of the ultrasound pulses.

7. The method according to claim 1, comprising controlling the phase of the ultrasound radiation by timely separating pulses of different phases in the sequence of pulses, the pulses presenting different parts of a common sinusoidal signal, such that each pulse starts with the ending phase of the preceding pulse.

8. The method according to claim 1, comprising controlling the phase of the electromagnetic radiation.

9. The method according to claim 1, wherein the analysis of the data comprises the steps of converting data indicative of the analog detected signals into digital data, reshaping the digital signal to thereby obtain a proper time series of data for each location, and performing a power spectrum operation on the time series.

10. The method according to claim 1, wherein the analysis of the data enables determination of information on absorbing substances in said region of interest.

11. The method according to claim 1, enabling monitoring of a temperature within the medium.

12. The method according to claim 11, wherein said monitoring comprises analyzing the data indicative of the detected modulated signals and generating data indicative of temperature mapping of the region of interest.

13. The method according to claim 1, wherein the imaging of the region of interest utilizing the interacting ultrasound and electromagnetic radiations enables obtaining a functional image of the region of interest, the method comprising:

transmitting ultrasound radiation to different locations inside the region of interest and detecting ultrasound radiation returned from said locations, to thereby obtain a structural image of said region of interest registered with the functional image.

14. An apparatus for detecting an effect of interactions of electromagnetic radiation with ultrasound radiation at different locations within a region of interest in a scattering medium to thereby enable imaging of said medium, the apparatus comprising:

(i) an ultrasound firing unit comprising a transducer arrangement operable to transmit a plurality of sequence of pulses of ultrasound radiation to a plurality of locations in said region of interest with an X-Y plane perpendicular to the axes of propagation of the ultrasound pulses; and an electromagnetic radiation source operable to illuminate said region of interest with incident electromagnetic radiation of at least one wavelength, to thereby produce signals of the electromagnetic radiation, each being frequency modulated by a frequency of the ultrasound radiation;

(ii) a phase control utility operable to affect the phase of the generated radiation;

(iii) a detector unit operable to detect said modulated signals and generate data indicative thereof; and (iv) a control unit for operating said ultrasound firing unit, said electromagnetic radiation source, and said phase control utility, the control unit comprising a data processing and analyzing utility for analyzing the data generated by the detector to enable said imaging;

the apparatus being characterized in that:

said ultrasound firing unit operates to provide each of said pulses of ultrasound radiation in the form of at least one sinusoidal cycle, said electromagnetic radiation source operates to produce said incident electromagnetic radiation in the form of a modulated continuous wave, and the control unit is operable to affect the phase of either the ultrasound radiation or the electromagnetic radiation to provide a phase continuity of the frequency modulated signals.

15. The apparatus according to claim 14, wherein said transducer arrangement comprises a single transducer displaceable within the X-Y plane.

16. The apparatus according to claim 14, wherein said transducer arrangement comprises a one-dimensional array of transducers aligned in a spaced-apart relationship along the X-axis, and being displaceable along the X-axis.

17. The apparatus according to claim 14, wherein said transducer arrangement comprises a two-dimensional array of transducers aligned in a spaced-apart relationship along the X- and Y-axes.

18. The apparatus according to claim 17, wherein said sequences of ultrasound pulses have different frequencies.

19. The apparatus according to claim 14, wherein said phase control utility is operable to control the phase of the ultrasound radiation such that the sequence of pulses comprises timely separated pulses of different phases.

20. The apparatus according to claim 19, wherein the pulses present different parts of a common sinusoidal signal, such that each pulse starts with an ending phase of a preceding pulse.

21. The apparatus according to claim 16, wherein said transducer arrangement comprises a multi-frequency phase array.

22. The apparatus according to claim 16, wherein said ultrasound firing unit comprises a beam shaping unit accommodated in the path of the ultrasound radiation for reducing a diameter of a spot excited in the medium by the ultrasound radiation, as compared to a diameter of a beam formed by all ultrasound radiation components generated by the transducers.

23. The apparatus according to claim 14, wherein said phase control unit is operable to control the phase of the electromagnetic radiation.

24. The apparatus according to claim 14, wherein said control unit comprises an analog to digital converter for processing analog output of the detector, and a data processing and analyzing utility operable to reshape a digital signal indicative of the detected signals to thereby obtain a proper time series of data for each location.

25. The apparatus according to claim 14, wherein the control unit is operable to selectively actuate the ultrasound firing unit, and both the ultrasound firing unit and the electromagnetic radiation source, signals detected during the operation of the ultrasound firing unit only being indicative of a structural image of the region of interest, and said modulated signals being indicative of a functional image of the region of interest.

26. The apparatus according to claim 14, wherein the detector unit comprises a CMOS camera for parallel detection of a plurality of the electromagnetic radiation components.

* * * * *